(12) United States Patent
Kato et al.

(10) Patent No.: US 6,218,558 B1
(45) Date of Patent: Apr. 17, 2001

(54) TRANSITION METAL COMPOUND, CATALYST COMPONENT FOR OLEFIN POLYMERIZATION AND PROCESS FOR THE PREPARATION OF α-OLEFIN POLYMER

(75) Inventors: Taku Kato; Sugio Nishimura, both of Kanagawa; Toshihiko Sugano, Mie, all of (JP)

(73) Assignee: Japan Polychem Corporation, Tokyo (JP)

( * ) Notice: Subject to any disclaimer, the term of this patent is extended or adjusted under 35 U.S.C. 154(b) by 0 days.

(21) Appl. No.: 09/327,684

(22) Filed: Jun. 8, 1999

(30) Foreign Application Priority Data

Jun. 8, 1998 (JP) .................................................. 10-158726

(51) Int. Cl.[7] .............................. C07F 17/00; C07F 7/00; B01J 31/00; C08F 4/64

(52) U.S. Cl. .................................. 556/12; 556/11; 556/28; 556/42; 556/53; 556/58; 526/127; 526/160; 526/943; 502/103; 502/117; 502/152

(58) Field of Search .............................. 556/11, 53, 42, 556/58, 28, 12; 502/103, 117, 152; 526/127, 160, 943

(56) References Cited

U.S. PATENT DOCUMENTS 6,084,043 * 7/2000 Sugano et al. ....................... 526/127

FOREIGN PATENT DOCUMENTS 0 846 696 A1 * 6/1998 (EP) .
0 963 996 A2 * 12/1999 (EP) .
WO98/31690 * 7/1998 (WO) .

* cited by examiner

Primary Examiner—Porfirio Nazario-Gonzalez
(74) Attorney, Agent, or Firm—Oblon, Spivak, McClelland, Maier & Neustadt, P.C.

(57) ABSTRACT

Disclosed are a novel transition metal compound represented by the following general formula (I), a catalyst component for olefin polymerization comprising same, a catalyst for olefin polymerization comprising said catalyst component, and a process for the preparation of an α-olefin polymer:

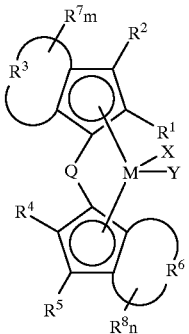

(I)

where the definition of formula (I) is described in the specification.

6 Claims, No Drawings

TRANSITION METAL COMPOUND, CATALYST COMPONENT FOR OLEFIN POLYMERIZATION AND PROCESS FOR THE PREPARATION OF α-OLEFIN POLYMER

FIELD OF THE INVENTION

The present invention relates to a novel transition metal compound, a catalyst component for α-olefin polymerization comprising the transition metal compound and a process for the preparation of an α-olefin polymer in the presence of the catalyst component. More particularly, the present invention relates to a highly active catalyst component which allows the preparation of a high molecular and high melting α-olefin polymer, a polymerization catalyst comprising such a catalyst component and a process for the preparation of an α-olefin polymer in the presence of such a catalyst.

BACKGROUND OF THE INVENTION

A so-called Kaminsky catalyst well known as uniform catalyst for olefin polymerization exhibits a high polymerization activity and thus allows the preparation of a polymer having a sharp molecular weight distribution.

As transition metal compounds for use in the preparation of an isotactic polyolefin in the presence of a Kaminsky catalyst there are known ethylenebis(indenyl)zirconium dichloride and ethylenebis(4,5,6,7-tetrahydroindenyl)zirconium dichloride (as in JP-A-61-130314 (The term "JP-A" as used herein means an "unexamined published Japanese patent application")). However, the preparation of a polyolefin in the presence of such a catalyst is normally disadvantageous in that the resulting polyolefin has a small molecular weight and, if low temperature polymerization is effected to obtain a polymer having an increased molecular weight, the catalyst exhibits a reduced polymerization activity.

Further, for the purpose of preparing a high molecular polyolefin, a method has been proposed involving the use of a hafnium compound instead of the foregoing zirconium compound (Journal of Molecular Catalysis, 56 (1989), pp. 237–247). However, this proposed method is disadvantageous in that the catalyst used exhibits a low polymerization activity.

Moreover, dimethylsilylene bis-substituted cyclopentadienyl zirconium dichloride has been proposed (as in JP-A-1-301704, Polymer Preprints, Japan 39 (1990), pp. 1,614–1,616, JP-A-3-12406). Dimethylsilylene bis(indenyl)zirconium dichloride has been proposed (as in JP-A-63-295007, JP-A-1-275609). The use of these compounds allows the preparation of a polymer having a high steric regularity and a high melting point in a relatively low temperature polymerization process but provides a polymer having a low steric regularity, melting point and molecular weight under high temperature polymerization conditions which are economical. On the other hand, a catalyst comprising a transition metal compound comprising halogen atoms introduced into substituents on the atoms crosslinking ligands and a co-catalyst has been proposed (as in JP-A-4-366106). However, such a catalyst is disadvantageous in that it provides a polymer having a low molecular weight and steric regularity as compared with similar catalysts free of halogen atoms.

Further, a compound has been known having enhanced isotacticity and increased molecular weight provided by adding substituents to indenyl group which is part of ligands (as in JP-A-4-268307, JP-A-6-157661). Moreover, a transition metal compound has been known wherein a subring containing two adjacent carbon atoms constituting a conjugated 5-membered ring has members other than 6 (as in JP-A-4-275294, JP-A-6-239914, JP-A-8-59724).

However, the foregoing compounds exhibit an insufficient catalytic action under high temperature polymerization conditions that are economical. Further, these compounds give a catalyst system soluble in the reaction medium in most cases. Accordingly, the resulting polymer has an amorphous grain form and a small bulk density and contains much fine powder and thus exhibits extremely poor grain properties. Accordingly, these compounds have many production disadvantages. For example, if these compounds are used in slurry polymerization or gas phase polymerization, continuous stable operation can be hardly conducted.

In order to solve these problems, on the other hand, a catalyst comprising a transition metal compound and/or organic aluminum compound supported on an inorganic oxide (e.g., silica, alumina) or organic material has been proposed (as in JP-A-61-108610, JP-A-60-135408, JP-A-61-296008, JP-A-3-74412, JP-A-3-74415). However, polymers prepared in the presence of such a catalyst contain much fine powder or coarse grains. Further, these polymers exhibit insufficient grain properties, e.g., low bulk density. Moreover, such a catalyst exhibits a low polymerization activity per unit solid component. Further, such a catalyst provides a polymer having a relatively low molecular weight and steric regularity than a catalyst system free of carrier. The present invention has been worked out under these circumstances.

SUMMARY OF THE INVENTION

An object of the present invention is to provide a novel transition metal compound which can form a catalyst component for α-olefin polymerization capable of producing a high molecular and high melting olefin polymer that can be extruded or injection-molded in a high yield.

Another object of the present invention is to provide a catalyst for α-olefin polymerization comprising the foregoing catalyst component and a process for the preparation of an α-olefin polymer in the presence of such a catalyst component.

A further object of the present invention is to provide a novel catalyst component which is little liable to deterioration of performance when used supported on a carrier to improve its process applicability.

A first aspect of the present invention lies in a novel transition metal compound represented by the following general formula (I):

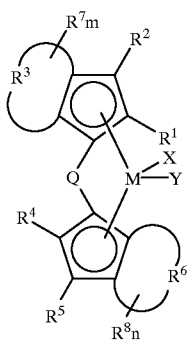 (I)

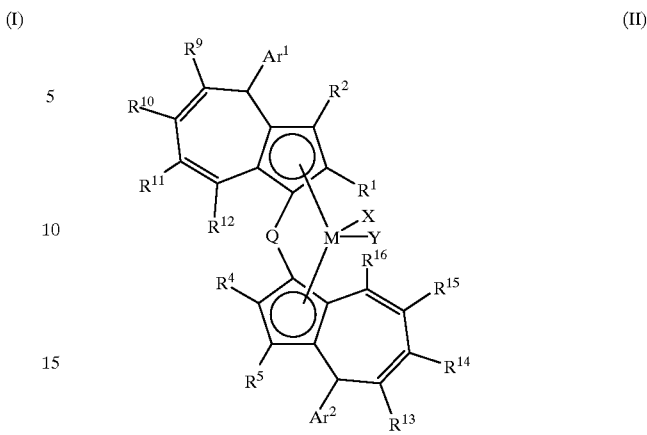 (II)

In the general formula (I), $R^1$, $R^2$, $R^4$ and $R^5$ each independently represent a hydrogen atom, $C_{1-10}$ hydrocarbon group, $C_{1-18}$ silicon-containing hydrocarbon group or $C_{1-18}$ halogenated hydrocarbon group.

$R^3$ and $R^6$ each independently represent a $C_{3-10}$ saturated or unsaturated divalent hydrocarbon group which is condensed with the 5-membered ring, with the proviso that at least one of $R^3$ and $R^6$ has from 5 to 8 carbon atoms and hence forms a 7- to 10-membered condensed ring.

$R^7$ and $R^8$ each independently represent a $C_{1-20}$ hydrocarbon group, $C_{7-30}$ oxygen-containing aryl group, $C_{7-30}$ nitrogen-containing aryl group or $C_{7-30}$ sulfur-containing aryl group, with the proviso that at least one of $R^7$ and $R^8$ is a $C_{7-30}$ oxygen-containing aryl group, $C_{7-30}$ nitrogen-containing aryl group or $C_{7-30}$ sulfur-containing aryl group.

The suffixes m and n each independently represent an integer of from 0 to 20, with the proviso that m and n are not 0 at the same time and if m or n is an integer of not less than 2, $R^7$'s or $R^8$'s may be connected to each other in arbitrary positions to form a new cyclic structure.

Q represents a divalent $C_{1-20}$ hydrocarbon group, halogenated hydrocarbon group or silylene, oligosilylene or germylene group which may have $C_{1-20}$ hydrocarbon or $C_{1-20}$ halogenated hydrocarbon group, which group connects the two 5-membered rings.

X and Y each independently represent a hydrogen atom, halogen atom, $C_{1-20}$ hydrocarbon group, $C_{1-20}$ silicon-containing hydrocarbon group, $C_{1-20}$ halogenated hydrocarbon group, $C_{1-20}$ oxygen-containing hydrocarbon group, amino group or $C_{1-20}$ nitrogen-containing hydrocarbon group.

M represents a transition metal element belonging to the groups 4 to 6 in the periodic table.

A second aspect of the present invention lies in a novel transition metal compound represented by the following general formula (II):

In the foregoing general formula (II), $R^1$ and $R^4$ each independently represent a $C_{1-6}$ hydrocarbon group, $C_{1-6}$ silicon-containing hydrocarbon group or $C_{1-6}$ halogenated hydrocarbon group.

$R^2$ and $R^5$ each independently represent a hydrogen atom or $C_{1-6}$ hydrocarbon group.

Q, N, X and Y are as defined in the general formula (II) $R^9$, $R^{10}$, $R^{11}$, $R^{12}$, $R^{13}$, $R^{14}$, $R^{15}$ an $R^{16}$ each independently represent a hydrogen atom or $C_{1-20}$ hydrocarbon group.

$Ar^1$ and $Ar^2$ each independently represent a $C_{7-30}$ oxygen-containing aryl group, $C_{7-30}$ nitrogen-containing aryl group or $C_{7-30}$ sulfur-containing aryl group.

A third aspect of the present invention lies in a catalyst component for α-olefin polymerization comprising a transition metal compound represented by the foregoing general formula (I) or (II).

A fourth aspect of the present invention lies in a catalyst for α-olefin polymerization comprising the following components (A) and (B) and optional component (C):

Component (A): Transition metal compound represented by the general formula (I) or (II);

Component (B): Compound selected from the group consisting of aluminumoxy compounds, ionic compounds capable of reacting with Component (A) to convert Component (A) to cation and Lewis acids; and Component (C): Particulate carrier A fifth aspect of the present invention lies in a catalyst for α-olefin polymerization comprising the following components (A) and (D) and optional component (E):

Component (A): Transition metal compound represented by the general formula (I) or (II);

Component (D): Compound selected from the group consisting of ion exchangeable layer compounds excluding silicate or inorganic silicates; and Component (E): Organic aluminum compound A sixth aspect of the present invention lies in a process for the preparation of an α-olefin polymer, which comprises allowing an α-olefin to come in contact with any one of the above-described catalysts to cause polymerization or copolymerization thereof.

DETAILED DESCRIPTION OF THE INVENTION

The present invention will be further described hereinafter. Firstly, the transition metal compound in the first aspect of the present invention will be described. The transition metal compound in the first aspect of the present invention is represented by the following general formula (I):

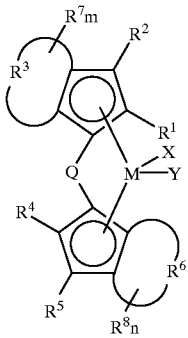

(I)

The transition metal compound in the first aspect of the present invention may be a compound (a) in which the 5-membered ring ligand containing substituents $R^1$, $R^2$ and $R^3$ and the 5-membered ring ligand containing substituents $R^4$, $R^5$ and $R^6$ are asymmetric with respect to a plane containing M, X and Y when viewed as to the relative positions thereof through the group Q, or a compound (b) in which the 5-membered ring ligand containing substituents $R^1$, $R^2$ and $R^3$ and the 5-membered ring ligand containing substituents $R^4$, $R^5$ and $R^6$ are symmetric with respect to a plane containing M, X and Y when viewed as to the relative positions thereof through the group Q.

However, in order to prepare a high molecular weight and high melting α-olefin polymer, it is preferred that the foregoing compound (a), i.e., compound in which the two 5-membered ring ligands do not have a relationship of real and mirror images with respect to the plane containing M, X and Y.

In the foregoing general formula (I), $R^1$, $R^2$, $R^4$ and $R^5$ each independently represent a hydrogen atom, $C_{1-10}$ hydrocarbon group, $C_{1-18}$ silicon-containing hydrocarbon group or $C_{1-18}$ halogenated hydrocarbon group.

Specific examples of the foregoing $C_{1-10}$ hydrocarbon group include alkyl group such as methyl, ethyl, n-propyl, i-propyl, n-butyl, i-butyl, s-butyl, t-butyl, n-pentyl, n-hexyl, cyclopropyl, cyclopentyl, cyclohexyl and methyl cyclohexyl, alkenyl group such as vinyl, propenyl and cyclohexenyl, arylalkyl group such as benzyl, phenylethyl and phenylpropyl, arylalkenyl group such as trans-styryl, and aryl group such as phenyl, tolyl, dimethylphenyl, ethylphenyl, trimethylphenyl, 1-naphthyl and 2-naphthyl.

Specific examples of the foregoing $C_{1-18}$ silicon-containing hydrocarbon group include trialkylsilyl group such as trimethylsilyl, triethylsilyl and t-butyldimethylsilyl, triarylsilyl group such as triphenylsilyl, (alkyl)(aryl)silyl group such as dimethylphenylsilyl group, and alkylsilylalkyl group such as bis(trimethylsilyl)methyl.

Examples of the halogen atom to be contained in the foregoing $C_{1-18}$ halogenated hydrocarbon group include fluorine atom, chlorine atom, bromine atom, and iodine atom. The foregoing halogenated hydrocarbon group, if the halogen atom is a fluorine atom, is a compound comprising the foregoing hydrocarbon group substituted by a fluorine atom in arbitrary positions. Specific examples of the halogenated hydrocarbon group include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, pentafluoropropyl, nonafluorobutyl, trifluorovinyl, 1,1-difluorobenzyl, 1,1,2,2-tetrafluorophenylethyl, 2-, 3-, 4-fluorophenyl, 2-, 3-, 4-chlorophenyl, 2-, 3-, 4-bromophenyl, 2,4-difluorophenyl, 3,5-difluorophenyl, 2,6-difluorophenyl, 2,5-difluorophenyl, 2,4-dichlorophenyl, 3,5-dichlorophenyl, 2,6-dichlorophenyl, 2,5-dichlorophenyl, 2,4,6-trifluorophenyl, 2,4,6-trichlorophenyl, pentafluorophenyl, pentachlorophenyl, 4-fluoronaphthyl, 4-chloronaphthyl, 2,4-difluoronaphthyl, heptafluoro-1-naphthyl, heptachloro-1-naphthyl, 2-, 3-, 4-trifluoromethylphenyl, 2-, 3-, 4-trichloromethylphenyl, 2,4-bis(trifluoromethyl)phenyl, 3,5-bis(trifluoromethyl)phenyl, 2,6-bis(trifluoromethyl)phenyl, 2,5-bis(trifluoromethyl)phenyl, 2,4-bis(trichloromethyl) phenyl, 3,5-bis(trichloromethyl)phenyl, 2,6-bis(trichloromethyl)phenyl, 2,5-bis(trichloromethyl)phenyl, 2,4,6-tris(trifluoromethyl)phenyl, 4-trifluoromethylnaphthyl, 4-trichloromethylnaphthyl, and 2,4-bis(trifluoromethyl)naphthyl.

Preferred among these groups represented by $R^1$ or $R^4$ is $C_{1-7}$ hydrocarbon group such as methyl, ethyl, propyl, butyl and benzyl.

The group represented by $R^2$ or $R^5$ is preferably a hydrogen atom.

(In the present specification, exemplified substituents are partly abbreviated. For example, the term "2-, 3-, 4-fluorophenyl" as mentioned above is meant to indicate three compounds, i.e., "2-fluorophenyl", "3-fluorophenyl", and "4-fluorophenyl".)

In the foregoing general formula (I), $R^3$ and $R^6$ each independently represent a $C_{3-10}$ saturated or unsaturated divalent hydrocarbon group which is condensed with the 5-membered ring, with the proviso that at least one of $R^3$ and $R^6$ has from 5 to 8 carbon atoms and hence forms a 7- to 10-membered condensed ring. It is preferred that both the two condensed rings be a 7- to 10-membered ring, more preferably a 7-membered ring.

Specific examples of the group represented by $R^3$ or $R^6$ include divalent saturated hydrocarbon group such as trimethylene, tetramethylene, pentamethylene, hexamethylene and heptamethylene, and divalent unsaturated hydrocarbon group such as propenylene, 2-butenylene, 1,3-butadienylene, 1-pentenylene, 2-pentenylene, 1,3-pentadienylene, 1,4-pentadienylene, 1-hexenylene, 2-hexenylene, 3-hexenylene, 1,3-hexadienylene, 1,4-hexadienylene, 1,5-hexadienylene, 2,4-hexadienylene, 2,5-hexadienylene and 1,3,5-hexatrienylene. Preferred among these groups are pentamethylene group, 1,3-pentadienylene group, 1,4-pentadienylene group, and 1,3,5-hexatrienylene group. Particularly preferred among these groups are 1,3-pentadienylene group and 1,4-pentadienylene group.

In the foregoing general formula (I), $R^7$ and $R^8$ each independently represent a $C_{1-20}$ hydrocarbon group, $C_{1-20}$ halogenated hydrocarbon group, $C_{7-30}$ oxygen-containing aryl group, $C_{7-30}$ nitrogen-containing aryl group or $C_{7-30}$ sulfur-containing aryl group, with the proviso that at least one of $R^7$ and $R^8$ is a $C_{7-30}$ oxygen-containing aryl group, $C_{7-30}$ nitrogen-containing aryl group or $C_{7-30}$ oxygen-containing aryl group.

Specific examples of the foregoing $C_{1-20}$ hydrocarbon group include alkyl group such as methyl, ethyl, n-propyl, i-propyl, n-butyl, i-butyl, s-butyl, t-butyl, n-pentyl, n-hexyl, cyclopropyl, cyclopentyl, cyclohexyl and methylcyclohexyl, alkenyl group such as vinyl, propenyl and cyclohexenyl, arylalkyl group such as benzyl, phenylethyl and phenylpropyl, arylalkenyl group such as trans-styryl, and aryl group such as phenyl, tolyl, dimethylphenyl, ethylphenyl, trimethylphenyl, 1-naphthyl, 2-naphthyl, acenaphthyl, phenanthryl and anthryl. Preferred among these hydrocarbon groups are $C_{1-4}$ alkyl group such as methyl, ethyl, n-propyl, i-propyl, n-butyl, i-butyl, s-butyl, t-butyl and cyclopropyl, and $C_{6-20}$ aryl group such as phenyl, tolyl, dimethylphenyl, ethylphenyl, trimethylphenyl, 1-naphthyl and 2-naphthyl.

Examples of the halogen atom to be contained in the foregoing $C_{1-20}$ halogenated hydrocarbon group include fluorine atom, chlorine atom, bromine atom and iodine atom. The foregoing halogenated hydrocarbon group is a compound comprising the foregoing hydrocarbon group substituted by a halogen atom in arbitrary positions. Specific examples of the $C_{1-20}$ halogenated hydrocarbon group employable herein include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, pentafluoropropyl, nonafluorobutyl, trifluorovinyl, 1,1-difluorobenzyl, 1,1,2,2-tetrafluorophenylethyl, 2-, 3-, 4-fluorophenyl, 2-, 3-, 4-chlorophenyl, 2-, 3-, 4-bromophenyl, 2,4-, 3,5-, 2,6-, 2,5-difluorophenyl, 2,4-, 3,5-, 2,6-, 2,5-dichlorophenyl, 2,4,6-trifluorophenyl, 2,4,6-trifluorophenyl, 2,4,6-trichlorophenyl, pentafluorophenyl, pentachlorophenyl, 4-fluoronaphthyl, 4-chloronaphthyl, 2,4-difluoronaphthyl, heptafluoro-1-naphthyl, heptachloro-1-naphthyl, 2-, 3-, 4-trifluoromethylphenyl, 2-, 3-, 4-trichloromethylphenyl, 2,4-, 3,5-, 2,6-, 2,5-bis(trifluoromethyl)phenyl, 2,4-, 3,5-, 2,6-, 2,5-bis(trichloromethyl)phenyl, 2,4,6-tris(trifluoromethyl)phenyl, 4-trifluoromethylnaphthyl, 4-trichloromethylnaphthyl, and 2,4-bis(trifluoromethyl)naphthyl.

Specific examples of the foregoing $C_{7-30}$ oxygen-containing aryl group include 2-, 3-, 4-methoxyphenyl, 2-, 3-, 4-ethoxyphenyl, 2-, 3-, 4-isopropoxyphenyl, 2-, 3-, 4-t-butoxyphenyl, 2-, 3-, 4-cyclohexyloxyphenyl, 2-, 3-, 4-phenoxyphenyl, 4-(2-fluorophenoxy)phenyl, 3-(3-fluorophenoxy)phenyl, 4-(4-trifluoromethylphenoxy)phenyl, 4-(4-nitrophenoxy)phenyl, 4-(4-methoxyphenoxy)phenyl, 3,4-dimethoxyphenyl, 3,4-(methylenedioxy)phenyl, 3-methyl-4-methoxyphenyl, 3,5-dimethyl-4-methoxyphenyl, 3,5-di-t-butyl-4-methoxyphenyl, 2-, 3-, 4-trimethylsiloxyphenyl, 2-, 3-, 4-t-butyldimethylsiloxyphenyl, 2-, 3-, 4-triphenylsiloxyphenyl, 4-(1-methoxyethyl)phenyl, 4-(1-t-butyldimethylsiloxyethyl)phenyl, 4-(1-methoxy-1-methylethyl)phenyl, 4-(1-t-butyl dimethylsiloxy-1-methylethyl)phenyl, 1-methoxy-5-indanyl, 1-t-butyldimethylsiloxy-5-indanyl, 1-methoxy-1-methyl-5-indanyl, 1-t-butyldimethylsiloxy-1-methyl-5-indanyl, 2-methoxy-1-naphthyl, 3-methoxy-1-naphthyl, 4-methoxy-1-naphthyl, 5-methoxy-1-naphthyl, 6-methoxy-1-naphthyl, 7-methoxy-1-naphthyl, 8-methoxy-1-naphthyl, 4-trimethylsiloxy-1-naphthyl, 5-trimethylsiloxy-1-naphthyl, 6-trimethylsiloxy-1-naphthyl, 7-trimethylsiloxy-1-naphthyl, 1-methoxy-2-naphthyl, 3-methoxy-2-naphthyl, 4-methoxy-2-naphthyl, 5-methoxy-2-naphthyl, 6-methoxy-2-naphthyl, 7-methoxy-2-naphthyl, 8-methoxy-2-naphthyl, 4-trimethylsiloxy-2-naphthyl, 5-trimethylsiloxy-2-naphthyl, 6-trimethylsiloxy-2-naphthyl, 7-trimethylsiloxy-2-naphthyl, 8-trimethylsiloxy-2-naphthyl, 4-t-butyldimethylsiloxy-2-naphthyl, 5-t-butyldimethylsiloxy-2-naphthyl, 6-t-butyldimethylsiloxy-2-naphthyl, 7-t-butyldimethylsiloxy-2-naphthyl, 8-t-butyldimethylsiloxy-2-naphthyl, 4-triphenylsiloxy-2-naphthyl, 2-naphthyl, 5-triphenylsiloxy-2-naphthyl, 6-triphenylsiloxy-2-naphthyl, 7-triphenylsiloxy-2-naphthyl, 8-triphenylsiloxy-2-naphthyl, 10-methoxy-9-anthryl, 3-methoxy-9-phenanthryl, 4-trimethylsiloxy-1-naphthacenyl, 4-t-butyldimethylsiloxy-1-naphthaceyl, 4'-methoxy-4-biphenylyl, 2',6'-dimethoxy-4-biphenylyl, and 2,6-dimethoxybiphenylyl.

Specific examples of the foregoing $C_{7-30}$ nitrogen-containing aryl group include 2-, 3-, 4-dimethylaminophenyl, 2-, 3-, 4-diethylaminophenyl, 2-, 3-, 4-diphenylaminophenyl, 3-methyl-4-dimethylaminophenyl, 4-dimethylamino-1-naphthyl, 4-dimethylamino-2-naphthyl, 5-dimethylamino-2-naphthyl, 6-dimethylamino-2-naphthyl, 7-dimethylamino-2-naphthyl, 3-dimethylamino-9-phenanthryl, and 3-diphenylamino-9-phenanthryl.

Specific examples of the foregoing $C_{7-30}$ sulfur-containing aryl group include compounds obtained by replacing the oxygen atom in the foregoing $C_{7-30}$ oxygen-containing aryl groups by sulfur atom.

In the foregoing general formula (I), m and n each independently represent an integer of from 0 to 20, particularly from 1 to 5. If m and/or n is an integer of from 2 to 20, the plurality of $R^7$'s ($R^8$'s) may be the same or different. However, m and n are not 0 at the same time. In other words, the divalent group $R^3$ and/or $R^6$ contains the foregoing substituent $R^7$ or $R^8$. Further, $R^7$ and/or $R^8$ is any of the foregoing $C_{7-30}$ oxygen-containing aryl, nitrogen-containing aryl or sulfur-containing aryl group. Preferred among these substituents is $C_{7-30}$ oxygen-containing aryl group.

If m or n is 2 or more, $R^7$'s or $R^8$'s may be connected to each other to form a new cyclic structure.

The position in which $R^7$ and $R^8$ are connected to $R^3$ and $R^6$ is not specifically limited. In practice, however, it is preferably the carbon adjacent to respective 5-membered ring (carbon in α-position).

In the foregoing general formula (I), Q represents a divalent $C_{1-20}$ group, halogenated $C_{1-20}$ hydrocarbon group or silylene, oligosilylene or germylene group which may have $C_{1-20}$ hydrocarbon or halogenated hydrocarbon group, which group connects the two 5-membered rings. If two hydrocarbon groups or halogenated hydrocarbon groups are present on the foregoing silylene group, oligosilylene group or germylene group, they may be connected to each other to form a cyclic structure.

Specific examples of the group represented by Q include alkylene group such as methylene, methyl methylene, dimethyl methylene, 1,2-ethylene, 1,3-trimethylene, 1,4-tetramethylene, 1,2-cyclohexylene and 1,4-cyclohexylene, arylalkylene group such as (methyl)(phenyl) methylene and diphenyl methylene, silylene group, alkylsilylene group such as methyl silylene, dimethyl silylene, diethyl silylene, di(n-propyl)silylene, di(i-propyl)silylene and di(cyclohexyl)silylene, (alkyl)(aryl)silylene group such as methylphenyl silylene and methyl(tolyl)silylene, (alkyl)(halogenated alkyl)silylene group such as methyl(chloromethyl)silylene, (alkyl)(halogenated aryl)silylene group such as (methyl)(4-fluorophenyl)silylene, halogenated alkylsilylene group such as bis(chloromethyl)silylene, alkyloligosilylene group such as tetramethyl disilylene, germylene group, alkylgermylene group obtained by replacing the silicon atom in the silylene group having the foregoing divalent $C_{1-20}$ hydrocarbon group by germanium, (alkyl)(aryl)germylene group, and arylgermylene group. Preferred among these groups are silylene group having $C_{1-20}$ hydrocarbon group and germylene group having $C_{1-20}$ hydrocarbon group. Particularly preferred among these groups are alkylsilylene group, (alkyl)(aryl)silylene group, and arylsilylene group.

In the foregoing general formula (I), X and Y each independently represent a hydrogen atom, halogen atom, $C_{1-20}$ hydrocarbon group, $C_{1-20}$ silicon-containing hydrocarbon group, $C_{1-20}$ halogenated hydrocarbon group, $C_{1-20}$ oxygen-containing hydrocarbon group, amino group or $C_{1-20}$ nitrogen-containing hydrocarbon group.

Examples of the foregoing halogen atom include fluorine atom, chlorine atom, bromine atom, and iodine atom. Examples of the foregoing $C_{1-20}$ hydrocarbon group and $C_{1-20}$ halogenated hydrocarbon group include those described above with reference to $R^7$ and $R^8$.

Examples of the $C_{1-20}$ oxygen-containing hydrocarbon group include alkoxyl group such as methoxy, ethoxy, propoxy, cyclopropoxy and butoxy, aryloxy group such as phenoxy, methylphenoxy, dimethylphenoxy and naphthoxy, and arylalkoxy group such as phenylmethoxy and naphthylmethoxy.

Examples of the $C_{1-20}$ nitrogen-containing hydrocarbon group include alkylamino group such as methylamino, dimethylamino, ethylamino and diethylamino, arylamino group such as phenylamino and diphenylamino, and (alkyl)(aryl) amino group such as (methyl)(phenyl) amino.

Specific examples of the foregoing $C_{1-20}$ silicon-containing hydrocarbon group include trialkylsilylmethyl group such as trimethylsilylmethyl and triethylsilylmethyl, and di(alkyl)(aryl) silylmethyl group such as dimethylphenyl silylmethyl, diethylphenylsilylmethyl and dimethyltolyl silylmethyl.

X and Y in the foregoing general formula (I) is preferably a hydrogen atom, halogen atom, $C_{1-20}$ hydrocarbon group or $C_{1-20}$ nitrogen-containing hydrocarbon group, more preferably a halogen atom, $C_{1-20}$ hydrocarbon group or $C_{1-20}$ nitrogen-containing hydrocarbon group, particularly a chlorine atom, methyl group, i-butyl group, phenyl group, dimethylamino group or diethylamino group.

In the foregoing general formula (I), M represents a transition metal element belonging to the groups 4 to 6 in the periodic table, preferably a transition metal element belonging to the group IV such as titanium, zirconium and hafnium, more preferably zirconium or hafnium.

The synthesis of the transition metal compound represented by the general formula (I) can be accomplished by any method depending on the substituents and how they are connected. A representative synthesis path is as shown in the following reaction formula. $H_2Ra$ and $H_2Rb$ in the following reaction formula have the following structural formulae:

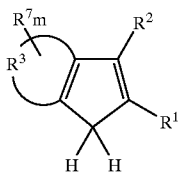

(H₂Ra)

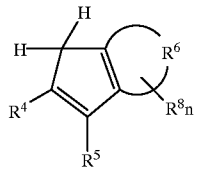

(H₂Rb)

wherein $R^1$ to $R^8$, n and m are as defined above.

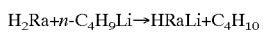
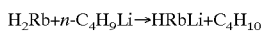
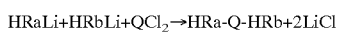
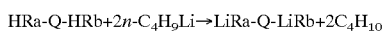
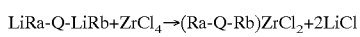

The production of the foregoing metal salt of cyclopentadienyl compound such as HRaLi and HRbLi may be accomplished by a synthesis method involving the addition reaction of alkyl group or aryl group as described in EP 697,418. In some detail, an alkyl lithium compound or aryl lithium compound is reacted with an azulene compound in an inert solvent to produce a lithium salt of dihydroazulenyl compound. As such an alkyl lithium compound there may be used methyl lithium, i-propyl lithium, n-butyl lithium, t-butyl lithium or the like. As such an aryl lithium compound there may be used a lithium compound containing the group represented by $R^7$ or $R^8$ in the general formula (I) such as phenyl lithium, 4-chlorophenyl lithium, 4-fluorophenyl lithium, 4-trifluoromethylphenyl lithium, naphthyl lithium, 4-methoxyphenyl lithium, 4-trimethylsiloxy phenyl lithium, 4-phenoxyphenyl lithium, 6-methoxy-2-naphthyl lithium and 6-t-butyldimethylsiloxy-2-naphthyl lithium. As the inert solvent there may be used hexane, benzene, toluene, diethyl ether and tetrahydrofuran, singly or in admixture.

The transition metal compound in the second aspect of the present invention will be described hereinafter. This compound is identified as a transition metal compound represented by the general formula (I) and is represented by the following general formula (II):

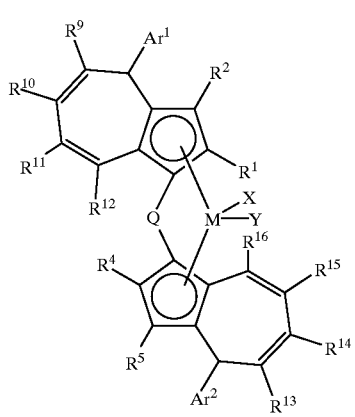

(II)

In the foregoing general formula (II), $R^1$ and $R^4$ each independently represent a $C_{1-6}$ hydrocarbon group, $C_{1-6}$ silicon-containing hydrocarbon group or $C_{1-6}$ halogenated hydrocarbon group.

Examples of the $C_{1-6}$ hydrocarbon group include alkyl group such as methyl, ethyl, n-propyl, i-propyl, n-butyl, i-butyl, s-butyl, t-butyl, n-pentyl, n-hexyl, cyclopropyl, cyclopentyl and cyclohexyl, alkenyl group such as vinyl, propenyl and cyclohexenyl, and phenyl group.

Examples of the $C_{1-6}$ silicon-containing hydrocarbon group include trialkylsilyl group such as trimethylsilyl group and triethylsilyl group.

Examples of the $C_{1-6}$ halogenated hydrocarbon group include halogenated alkyl group such as fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, pentafluoropropyl and nonafluorobutyl, and halogenated phenyl group such as 2-, 3-, 4-chlorophenyl, 2,4-, 3,5-, 2,6-, 2,5-dichlorophenyl, 2,4,6-trichlorophenyl and pentachlorophenyl.

Preferred among these groups are $C_{1-6}$ hydrocarbon groups. Particularly preferred among these $C_{1-6}$ hydrocarbon groups are methyl, ethyl, n-propyl, i-propyl, n-butyl, i-butyl, n-pentyl, n-hexyl, and cyclopropyl.

In the foregoing general formula (II), $R^2$ and $R^5$ each independently represent a hydrogen atom or $C_{1-6}$ hydrocarbon group.

Specific examples of the $C_{1-6}$ hydrocarbon group include those exemplified above with reference to $R^1$ and $R^4$.

In the foregoing general formula (II), $R^2$ and $R^5$ each are preferably a hydrogen atom.

In the foregoing general formula (II), Q, M, X and Y are as defined above.

In the foregoing general formula (II), $R^9$, $R^{10}$, $R^{11}$, $R^{12}$, $R^{13}$, $R^{14}$, $R^{15}$ and $R^{16}$ each independently represent a hydrogen atom or $C_{1-20}$ hydrocarbon group.

The $C_{1-20}$ hydrocarbon group may be the same as that in the general formula (I). In the general formula (II), $R^9$, $R^{10}$, $R^{11}$, $R^{12}$, $R^{13}$, $R^{14}$, $R^{15}$ and $R^{16}$ each are a hydrogen atom, methyl group, ethyl group, isopropyl group, phenyl group or the like.

In the foregoing general formula (II), $Ar^1$ and $Ar^2$ each independently represent a $C_{7-30}$ oxygen-containing aryl group, $C_{7-30}$ nitrogen-containing aryl group or $C_{7-30}$ sulfur-containing aryl group. Specific examples of the $C_{7-30}$ oxygen-containing aryl group, $C_{7-30}$ nitrogen-containing aryl group or $C_{7-30}$ sulfur-containing aryl group include those exemplified with reference to the general formula (I). Preferred among these groups is oxygen-containing aryl group.

The oxygen-containing aryl groups represented by the general formulae (III) and (IV) will be described hereinafter. These groups are identified as oxygen-containing aryl group in the transition metal compound represented by the general formula (I) or (II):

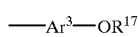

(III)

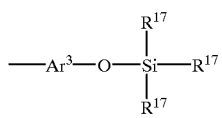

(IV)

In the foregoing general formulae (III) and (IV), $Ar^3$ represents a $C_{6-18}$ aryl group. Specific examples of the $C_{6-18}$ aryl group include phenyl group, tolyl group, xylyl group, mesityl group, biphenylyl group, naphthyl group, methyl naphthyl group, dimethyl naphthyl group, anthryl group, phenanthryl group, triphenylenyl group, pyrenyl group, chrysenyl group, and naphthacenyl group.

In the foregoing general formulae (III) and (IV), $R^{17}$ represents a hydrogen atom, $C_{1-6}$ alkyl group, $C_{3-6}$ cycloalkyl group, $C_{6-10}$ aryl group, $C_{6-10}$ halogen-containing aryl group, $C_{6-10}$ nitro group-containing aryl group or $C_{7-14}$ alkoxy group-containing aryl group. The plurality of $R^{17}$'s may be the same or different.

Specific examples of the $C_{1-6}$ alkyl group include methyl, ethyl, n-propyl, i-propyl, n-butyl, i-butyl, s-butyl, t-butyl, n-pentyl, and n-hexyl.

Specific examples of the $C_{3-6}$ cycloalkyl group include cyclopropyl, cyclopentyl, and cyclohexyl.

Specific examples of the $C_{6-10}$ aryl group include phenyl group, tolyl group, xylyl group, mesityl group, and naphthyl group.

Specific examples of the $C_{6-10}$ halogen-containing aryl group include 2-, 3-, 4-fluorophenyl, 2-, 3-, 4-chlorohenyl, 2-, 3-, 4-bromophenyl, 2,4-, 3,5-, 2,6-, 2,5-difluorophenyl, 2,4-, 3,5-, 2,6-, 2,5-dichlorophenyl, 2,4,6-trifluorophenyl, 2,4,6-trichlorophenyl, pentafluorophenyl, pentachlorophenyl, 4-fluoronaphthyl, 4-chloronaphthyl, and 2,4-difluoronaphthyl.

Specific examples of the $C_{6-10}$ nitro group-containing aryl group include 4-nitrophenyl group, and 6-nitronaphthyl group.

Specific examples of the $C_{7-14}$ alkoxy group-containing aryl group include 4-methoxyphenyl group, 3-methoxyphenyl group, 3,5-dimethoxyphenyl group, 4-methoxynaphthyl group, and 6-methoxynaphthyl group.

Specific examples of the transition metal compound of the present invention will be given below. Although these exemplified compounds are merely designated by chemical name, they are in both asymmetric and symmetric forms from the standpoint of stereostructure. For the understanding of nomenclature of the following exemplified compounds, the structural formula of the zirconium dichloride (1) will be given below.

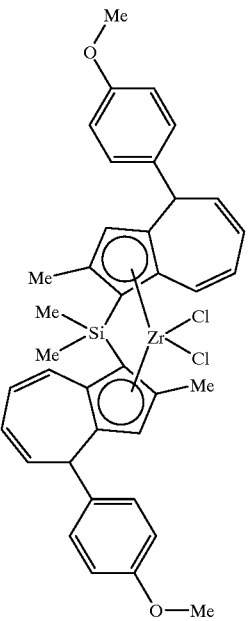

(1) Dichloro{1,1'-dimethylsilylenebis[2-methyl-4-(4-methoxyphenyl)-4H-azulenyl]}zirconium
(2) Dichloro{1,1'-dimethylsilylenebis[2-methyl-4-(3-methoxyphenyl)-4H-azulenyl]}zirconium (3) Dichloro{1,1'-dimethylsilylenebis[2-methyl-4-(2-methoxyphenyl)-4H-azulenyl]}zirconium
(4) Dichloro{1,1'-dimethylsilylenebis[2-ethyl-4-(3-methyl-4-methoxyphenyl)-4H-azulenyl]}zirconium
(5) Dichloro{1,1'-dimethylsilylenebis[2-methyl-4-(3,5-dimethyl-4-methoxyphenyl)-4H-azulenyl]}zirconium
(6) Dichloro{1,1'-dimethylsilylenebis[2-isopropyl-4-(3,5-dimethyl-4-methoxyphenyl)-4H-azulenyl]}zirconium
(7) Dichloro{1,1'-dimethylsilylenebis[2-methyl-4-(3,5-di-t-butyl-4-methoxyphenyl)-4H-azulenyl]}zirconium
(8) Dichloro{1,1'-dimethylsilylenebis{2-methyl-4-[3,4-(methylenedioxy)phenyl]-4H-azulenyl}]zirconium
(9) Dichloro{1,1'-dimethylsilylenebis[2-methyl-4-(4-phenoxyphenyl]-4H-azulenyl]}zirconium
(10) Dichloro{1,1'-dimethylsilylenebis[2-methyl-4-(4-phenoxyphenyl]-6-isopropyl-4H-azulenyl]}zirconium
(11) Dichloro{1,1'-dimethylsilylenebis[2-phenyl-4-(4-phenoxyphenyl]-4H-azulenyl]}zirconium
(12) Dichloro{1,1'-dimethylsilylenebis[2-methyl-4-(4-trimethylsiloxyphenyl]-4H-azulenyl]}zirconium
(13) Dichloro{1,1'-dimethylsilylenebis[2-n-propyl-4-(3-trimethylsiloxyphenyl]-4H-azulenyl]}zirconium
(14) Dichloro{1,1'-dimethylsilylenebis[2-methyl-4-(4-t-butyldimethylsiloxyphenyl]-4H-azulenyl]}zirconium
(15) Dichloro{1,1'-dimethylsilylenebis[2-ethyl-4-(4-t-butyldimethylsiloxyphenyl]-4H-azulenyl]}zirconium
(16) Dichloro{1,1'-dimethylsilylenebis[2-methyl-4-(4-triphenylsiloxyphenyl]-4H-azulenyl]}zirconium
(17) Dichloro{1,1'-dimethylsilylenebis[2-methyl-4-(2-methoxy-1-naphthyl)-4H-azulenyl]}zirconium
(18) Dichloro{1,1'-dimethylsilylenebis[2-methyl-4-(3-methoxy-1-naphthyl)-4H-azulenyl]}zirconium
(19) Dichloro{1,1'-dimethylsilylenebis[2-methyl-4-(4-methoxy-1-naphthyl)-4H-azulenyl]}zirconium
(20) Dichloro{1,1'-dimethylsilylenebis[2-methyl-4-(5-methoxy-1-naphthyl)-4H-azulenyl]}zirconium
(21) Dichloro{1,1'-dimethylsilylenebis[2-methyl-4-(6-methoxy-1-naphthyl)-4H-azulenyl]}zirconium
(22) Dichloro{1,1'-dimethylsilylenebis[2-methyl-4-(7-methoxy-1-naphthyl)-4H-azulenyl]}zirconium
(23) Dichloro{1,1'-dimethylsilylenebis[2-methyl-4-(8-methoxy-1-naphthyl)-4H-azulenyl]}zirconium
(24) Dichloro{1,1'-dimethylsilylenebis[2-methyl-4-(3-tri-n-butylsiloxy-1-naphthyl)-4H-azulenyl]}zirconium
(25) Dichloro{1,1'-dimethylsilylenebis[2-methyl-4-(4-trimethylsiloxy-1-naphthyl)-4H-azulenyl]}zirconium
(26) Dichloro{1,1'-dimethylsilylenebis[2-methyl-4-(5-trimethylsiloxy-1-naphthyl)-4H-azulenyl]}zirconium
(27) Dichloro{1,1'-dimethylsilylenebis[2-methyl-4-(6-trimethylsiloxy-1-naphthyl)-4H-azulenyl]}zirconium
(28) Dichloro{1,1'-dimethylsilylenebis[2-methyl-4-(7-triethylsiloxy-1-naphthyl)-4H-azulenyl]}zirconium
(29) Dichloro{1,1'-dimethylsilylenebis[2-methyl-4-(1-ethoxy-2-naphthyl)-4H-azulenyl]}zirconium
(30) Dichloro{1,1'-dimethylsilylenebis[2-methyl-4-(3-t-butoxy-2-naphthyl)-4H-azulenyl]}zirconium
(31) Dichloro{1,1-dimethylsilylenebis[2-methyl-4-(4-cyclopropoxy-2-naphthyl)-4H-azulenyl]}zirconium
(32) Dichloro{1,1'-dimethylsilylenebis[2-methyl-4-(5-phenoxy-2-naphthyl)-4H-azulenyl]}zirconium
(33) Dichloro{1,1'-dimethylsilylenebis[2-methyl-4-(6-methoxy-2-naphthyl)-4H-azulenyl]}zirconium
(34) Dichloro{1,1'-dimethylsilylenebis[2-methyl-4-(6-methoxy-2-naphthyl)-7-isopropyl-4H-azulenyl]}zirconium
(35) Dichloro{1,1'-dimethylsilylenebis[2-ethyl-4-(6-methoxy-2-naphthyl)-4H-azulenyl]}zirconium
(36) Dichloro{1,1'-dimethylsilylenebis[2-i-propyl-4-(6-methoxy-2-naphthyl)-4H-azulenyl]}zirconium
(37) Dichloro{1,1-dimethylsilylenebis[2-methyl-4-(6-isopoxy-2-naphthyl)-4H-azulenyl]}zirconium
(38) Dichloro{1,1'-dimethylsilylenebis[2-methyl-4-(7-naphthoxy-2-naphthyl)-4H-azulenyl]}zirconium
(39) Dichloro{1,1'-dimethylsilylenebis[2-methyl-4-(8-methoxy-2-naphthyl)-4H-azulenyl]}zirconium
(40) Dichloro{1,1'-dimethylsilylenebis[2-methyl-4-(6-trimethylsiloxy-2-naphthyl)-4H-azulenyl]}zirconium
(41) Dichloro{1,1'-dimethylsilylenebis[2-ethyl-4-(6-triethylsiloxy-2-naphthyl)-4H-azulenyl]}zirconium
(42) Dichloro{1,1'-dimethylsilylenebis[2-i-propyl-4-(6-tri-n-butylsiloxy-2-naphthyl)-4H-azulenyl]}zirconium
(43) Dichloro{1,1'-dimethylsilylenebis[2-methyl-4-(6-t-butyldimethylsiloxy-2-naphthyl)-4H-azulenyl]} zirconium
(44) Dichloro{1,1'-dimethylsilylenebis[2-ethyl-4-(6-t-butyldimethylsiloxy-2-naphthyl)-4H-azulenyl]} zirconium
(45) Dichloro{1,1'-dimethylsilylenebis[2-i-propyl-4-(6-t-butyldimethylsiloxy-2-naphthyl)-4H-azulenyl]} zirconium
(46) Dichloro{1,1'-dimethylsilylenebis[2-cyclopropyl-4-(6-t-butyldimethylsiloxy-2-naphthyl)-4H-azulenyl]} zirconium
(47) Dichloro{1,1'-dimethylsilylenebis[2-methyl-4-(6-triphenylsiloxy-2-naphthyl)-4H-azulenyl]}zirconium
(48) Dichloro{1,1'-dimethylsilylenebis[2-methyl-4-(10-methoxy-9-anthryl)-4H-azulenyl]}zirconium
(49) Dichloro{1,1'-dimethylsilylenebis[2-ethyl-4-(10-methoxy-9-anthryl)-4H-azulenyl]}zirconium
(50) Dichloro{1,1'-dimethylsilylenebis[2-i-propyl-4-(10-methoxy-9-anthryl)-4H-azulenyl]}zirconium
(51) Dichloro{1,1'-dimethylsilylenebis[2-cyclopropyl-4-(10-methoxy-9-anthryl)-4H-azulenyl]}zirconium
(52) Dichloro{1,1'-dimethylsilylenebis[2-methyl-4-(3-methoxy-9-phenanthryl)-4H-azulenyl]}zirconium
(53) Dichloro{1,1'-dimethylsilylenebis[2-methyl-4-(4-t-butyldimethylsiloxy-1-naphthacenyl)-4H-azulenyl]} zirconium
(54) Dichloro{1,1'-dimethylsilylenebis[2-methyl-4-(4'-methoxy-4-biphenylyl)-4H-azulenyl]}zirconium
(55) Dichloro{1,1'-dimethylsilylenebis{2-methyl-4-[4-(1-methoxyethyl)phenyl]-4H-azulenyl})zirconium
(56) Dichloro(1,1'-dimethylsilylenebis{2-methyl-4-[4-(1-methoxy-1-methylethyl)phenyl]-4H-azulenyl})zirconium
(57) Dichloro(1,1'-dimethylsilylenebis{2-methyl-4-[4-(1-t-butyldimethylsiloxyethyl)phenyl]-4H-azulenyl}) zirconium
(58) Dichloro(1,1'-dimethylsilylenebis{2-methyl-4-[4-(1-t-butyldimethylsiloxy-1-methylethyl)phenyl]-4H-azulenyl})zirconium
(59) Dichloro{1,1'-dimethylsilylenebis[2-methyl-4-(1-methoxy-5-indanyl)-4H-azulenyl})zirconium
(60) Dichloro{1,1'-dimethylsilylenebis[2-methyl-4-(1-methoxy-1-methyl-5-indanyl)-4H-azulenyl]}zirconium
(61) Dichloro{1,1'-dimethylsilylenebis[2-methyl-4-(1-t-butyldimethylsiloxy-5-indanyl)-4H-azulenyl]}zirconium
(62) Dichloro{1,1'-dimethylsilylenebis[2-methyl-4-(1-t-butyldimethylsiloxy-1-methyl-5-indanyl)-4H-azulenyl]} zirconium
(63) Dichloro{1,1'-dimethylsilylenebis[2-methyl-4-(4-methoxyphenyl)-4H-5,6,7,8-tetrahydroazulenyl]} zirconium
(64) Dichloro{1,1'-ethylmethylsilylenebis[2-methyl-4-(4-phenoxyphenyl)-4H-5,6,7,8-tetrahydroazulenyl]} zirconium

(65) Dichloro{1,1'-ethylmethylsilylenebis[2-methyl-4-(4-trimethylsiloxyphenyl)-4H-5,6,7,8-tetrahydroazulenyl]}zirconium
(66) Dichloro{1,1'-diethylsilylenebis[2-methyl-4-(4-t-butyldimethylsiloxyphenyl)-4H-5,6,7,8-tetrahydroazulenyl]}zirconium
(67) Dichloro{1,1'-dimethylsilylenebis[2-methyl-4-(6-methoxy-2-naphthyl)-4H-5,6,7,8-tetrahydroazulenyl]}zirconium
(68) Dichloro{1,1'-dimethylsilylenebis[2-methyl-4-(6-t-butyldimethylsiloxy-2-naphthyl)-4H-5,6,7,8-tetrahydroazulenyl]}zirconium
(69) Dichloro{1,1'-dimethylsilylenebis[2-methyl-4-(10-ethoxy-9-anthryl)-4H-5,6,7,8-tetrahydroazulenyl]}zirconium
(70) Dichloro{1,1'-dimethylsilylenebis[2-methyl-4-(4'-cyclopropoxy-4-biphenylyl)-4H-5,6,7,8-tetrahydroazulenyl]}zirconium
(71) Dichloro{1,1'-ethylmethylsilylenebis[2-methyl-4-(4-methoxyphenyl)-4H-azulenyl]}zirconium
(72) Dichloro{1,1'-ethylmethylsilylenebis[2-methyl-4-(4-phenoxyphenyl)-4H-azulenyl]}zirconium
(73) Dichloro{1,1'-ethylmethylsilylenebis[2-methyl-4-(4-trimethylsiloxyphenyl)-4H-azulenyl]}zirconium
(74) Dichloro{1,1'-diethylsilylenebis[2-methyl-4-(4-t-butyldimethylsiloxyphenyl)-4H-azulenyl]}zirconium
(75) Dichloro{1,1'-diethylsilylenebis[2-methyl-4-(6-methoxy-2-naphthyl)-4H-azulenyl]}zirconium
(76) Dichloro{1,1'-diethylsilylenebis[2-methyl-4-(6-t-butyldimethylsiloxy-2-naphthyl)-4H-azulenyl]}zirconium
(77) Dichloro{1,1'-diethylsilylenebis[2-methyl-4-(10-methoxy-9-anthryl)-4H-azulenyl]}zirconium
(78) Dichloro{1,1'-diethylsilylenebis[2-methyl-4-(4'-methoxy-4-biphenylyl)-4H-azulenyl]}zirconium
(79) Dichloro{1,1'-(methyl)(phenethyl)silylenebis[2-methyl-4-(4-methoxyphenyl)-4H-azulenyl]}zirconium
(80) Dichloro{1,1'-(methyl)(naphthyl)silylenebis[2-methyl-4-(4-phenoxyphenyl)-4H-azulenyl]}zirconium
(81) Dichloro{1,1'-(methyl)(naphthylethyl)silylenebis[2-methyl-4-(4-trimethylsiloxyphenyl)-4H-azulenyl]}zirconium
(82) Dichloro{1,1'-(methyl)(phenyl)silylenebis[2-methyl-4-(4-t-butyldimethylsiloxyphenyl)-4H-azulenyl]}zirconium
(83) Dichloro{1,1'-(methyl)(4-fluorophenyl)silylenebis[2-methyl-4-(6-methoxy-2-naphthyl)-4H-azulenyl]}zirconium
(84) Dichloro{1,1'- (methyl)(phenyl)silylenebis[2-methyl-4-(6-t-butyldimethylsiloxy-2-naphthyl)-4H-azulenyl]}zirconium
(85) Dichloro{1,1'-(methyl)(phenyl)silylenebis[2-methyl-4-(10-methoxy-9-anthryl)-4H-azulenyl]}zirconium
(86) Dichloro{1,1'-(methyl)(4-chlorophenyl)silylenebis[2-methyl-4-(4'-methoxy-4-biphenylyl)-4H-azulenyl]}zirconium
(87) Dichloro{1,1'-tetramethylenesilylenebis[2-methyl-4-(4-methoxyphenyl)-4H-azulenyl]}zirconium
(88) Dichloro{1,1'-tetramethylenesilylenebis2-methyl-4-(4-phenoxyphenyl)-4H-azulenyl]}zirconium
(89) Dichloro{1,1'-pentamethylenesilylenebis[2-methyl-4-(4-trimethylsiloxyphenyl)-4H-azulenyl]}zirconium
(90) Dichloro{1,1'-trimethylenesilylenebis[2-methyl-4-(4-t-butyldimethylsiloxyphenyl)-4H-azulenyl]}zirconium
(91) Dichloro{1,1'-trimethylenesilylenebis[2-methyl-4-(6-methoxy-2-naphthyl)-4H-azulenyl]}zirconium
(92) Dichloro{1,1'-trimethylenesilylenebis[2-methyl-4-(6-t-butyldimethylsiloxy-2-naphthyl)-4H-azulenyl]}zirconium
(93) Dichloro{1,1'-trimethylenesilylenebis[2-methyl-4-(10-methoxy-9-anthryl)-4H-azulenyl]}zirconium
(94) Dichloro{1,1'-trimethylenesilylenebis[2-methyl-4-(4'-methoxy-4-biphenylyl)-4H-azulenyl]}zirconium
(95) Dichloro{1,1'-[1,2-tetramethyldisilanediyl]bis[2-methyl-4-(4-methoxyphenyl)-4H-azulenyl]}zirconium
(96) Dichloro{1,1'-dimethylgermylenebis[2-methyl-4-(4-phenoxyphenyl)-4H-azulenyl]}zirconium
(97) Dichloro{1,1'-ethylgermylenebis[2-methyl-4-(4-trimethylsiloxyphenyl)-4H-azulenyl]}zirconium
(98) Dichloro{1,1'-(methyl)(phenyl)germylenebis[2-methyl-4-(4-t-butyldimethylsiloxyphenyl)-4H-azulenyl]}zirconium
(99) Dichloro{1,1'-dimethylgermylenebis[2-methyl-4-(6-methoxy-2-naphthyl)-4H-azulenyl]}zirconium
(100) Dichloro{1,1'-dimethylgermylenebis[2-methyl-4-(6-t-butyldimethylsilyloxy-2-naphthyl)-4H-azulenyl]}zirconium
(101) Dichloro{1,1'-diphenylgermylenebis[2-methyl-4-(10-methoxy-9-anthryl)-4H-azulenyl]}zirconium
(102) Dichloro{1,1'-n-propylmethylgermylenebis[2-methyl-4-(4'-methoxy-4-biphenylyl)-4H-azulenyl]}zirconium
(103) Dichloro{1,1'-dimethylmethylenebis[2-methyl-4-(4-methoxyphenyl)-4H-azulenyl]}zirconium
(104) Dichloro{1,1'-dimethylmethylenebis[2-methyl-4-(4-phenoxyphenyl)-4H-azulenyl]}zirconium
(105) Dichloro{1,1'-dimethylmethylenebis[2-methyl-4-(4-trimethylsiloxyphenyl)-4H-azulenyl]}zirconium
(106) Dichloro{1,1'-ethylenebis[2-methyl-4-(4-t-butyldimethylsiloxyphenyl)-4H-azulenyl]}zirconium
(107) Dichloro{1,1'-ethylenebis[2-methyl-4-(6-methoxy-2-naphthyl)-4H-azulenyl]}zirconium
(108) Dichloro{1,1'-ethylenebis[2-methyl-4-(6-t-butyldimethylsiloxy-2-naphthyl)-4H-azulenyl]}zirconium
(109) Dichloro{1,1'-[1,2-dimethylethylene]bis[2-methyl-4-(10-methoxy-9-anthryl)-4H-azulenyl]}zirconium
(110) Dichloro{1,1'-[1,2-dimethylethylene]bis[2-methyl-4-(4'-methoxy-4-biphenylyl)-4H-azulenyl]}zirconium
(111) Dichloro{1,1'-[1,2-cyclohexylene]bis[2-methyl-4-(4-methoxyphenyl)-4H-azulenyl]}zirconium
(112) Dichloro{1,1'-trimethylenebis[2-methyl-4-(4-phenoxyphenyl)-4H-azulenyl]}zirconium
(113) Dichloro{1,1'-[1,4-cyclohexylene]bis[2-methyl-4-(4-trimethylsiloxyphenyl)-4H-azulenyl]}zirconium
(114) Dichloro{1,1'-trimethylenebis[2-methyl-4-(4-t-butyldimethylsiloxyphenyl)-4H-azulenyl]}zirconium
(115) Dichloro{1,1'-trimethylenebis[2-methyl-4-(6-methoxy-2-naphthyl)-4H-azulenyl]}zirconium
(116) Dichloro{1,1'-trimethylenebis[2-methyl-4-(6-t-butyldimethylsiloxy-2-naphthyl)-4H-azulenyl]}zirconium
(117) Dichloro{1,1'-[1,2-phenylene]bis[2-methyl-4-(10-methoxy-9-anthryl)-4H-azulenyl]}zirconium
(118) Dichloro{1,1'-[1,2-phenylene]bis[2-methyl-4-(4'-methoxy-4-biphenylyl)-4H-azulenyl]}zirconium
(119) Dichloro{dimethylsilylene-1-[2-methyl-4-(4-phenoxyphenyl)-4H-azulenyl]-1-[2-methyl-4-phenylindenyl]}zirconium
(120) Dichloro{dimethylsilylene-1-[2-methyl-4-(4-trimethylsiloxyphenyl)-4H-5,6,7,8-tetrahydroazulenyl]-1-[2-methyl-4-phenylindenyl]}zirconium
(121) Dichloro{diethylsilylene-1-[2-methyl-4-(4-t-butyldimethylsiloxyphenyl)-4H-azulenyl]-1-[2-methyl-4-naphthylindenyl]}zirconium
(122) Dichloro{dimethylsilylene-1-[2-methyl-4-(6-methoxy-2-naphthyl)-4H-azulenyl]-1-(2-ethyl-4-phenylindenyl]}zirconium (123) Dichloro{dimethylsilylene-1-[2-methyl-4-(6-t-butyldimethylsiloxy-2-naphthyl)-4H-azulenyl]-1-[2-ethyl-4-naphthylindenyl]}zirconium
(124) Dichloro{dimethylsilylene-1-[2-methyl-4-(10-ethoxy-9-anthryl)-4H-azulenyl]-1-[2-methyl-4,5-benzindenyl]}zirconium
(125) Dichloroldimethylsilylene-1-[2-methyl-4-(4'-cyclopropoxy-4-biphenylyl)-4H-azulenyl]-1-[2-n-propyl-4-phenanthrylindenyl]}zirconium
(126) Dichloro{1,1'-dimethylsilylenebis[2-methyl-4-(4-dimethylaminophenyl)-4H-azulenyl]}zirconium
(127) Dichloro{1,1'-dimethylsilylenebis[2-methyl-4-(4-diethylaminophenyl)-4H-azulenyl]}zirconium
(128) Dichloro{1,1'-dimethylsilylenebis[2-methyl-4-(3-methyl-4-dimethylaminophenyl)-4H-azulenyl]}zirconium
(129) Dichloro{1,1'-dimethylsilylenebis[2-ethyl-4-(6-dimethylamino-2-naphthyl)-4H-azulenyl]}zirconium
(130) Dichloro{1,1'-dimethylsilylenebis[2-methyl-4-(4-methylthiophenyl)-4H-azulenyl]}zirconium
(131) Dichloro{1,1'-dimethylsilylenebis[2-methyl-4-(4-ethylthiophenyl)-4H-azulenyl]}zirconium
(132) Dichloro{1,1'-dimethylsilylenebis[2-methyl-4-(4-phenylthiophenyl)-4H-azulenyl]}zirconium
(133) Dichloro{1,1'-dimethylsilylenebis[2-methyl-4-(4-trimethylsilylthiophenyl)-4H-azulenyl]}zirconium
(134) Dichloro{1,1'-dimethylsilylenebis[2-methyl-4-(4-trimethylsilylthio-2-naphthyl)-4H-azulenyl]}zirconium There may be further exemplified compounds obtained by replacing one or both of the chlorine atoms constituting Y and Y moiety in the foregoing general formula (I) or (II) by hydrogen atom, fluorine atom, bromine atom, iodine atom, methyl group, phenyl group, fluorophenyl group, benzyl group, methoxy group, dimethylamino group, diethylamino group, etc. Moreover, compounds obtained by replacing zirconium as central metal (M) in the foregoing exemplified compound by titanium, hafnium, tantalum, niobium, vanadium, tungsten, molybdenum, etc. may be exemplified. Preferred among these compounds are compounds of transition metal belonging to the group IV such as zirconium, titanium and hafnium. Particularly preferred among these transition metals are zirconium and hafnium.

The catalysts for α-olefin polymerization (1) and (2) of the present invention will be described hereinafter. All these catalysts comprise the foregoing transition metal compound of the present invention incorporated therein as a component (A).

Firstly, the catalyst for α-olefin polymerization (1) of the present invention will be further described. This catalyst comprises as a component (B) an aluminumoxy compound, ionic compound capable of reacting with the component (A) to convert the component (A) to cation or Lewis acid, and a particulate carrier as an optional component (C). Some of these Lewis acids can be grasped as ionic compounds capable of reacting with the component (A) to convert the component (A) to cation. Accordingly, it can be interpreted that a compound belonging to both the foregoing Lewis acid and ionic compound belongs to any one of the two groups.

Specific examples of the foregoing aluminumoxy compound include compounds represented by the following general formulae (V), (VI) and (VII):

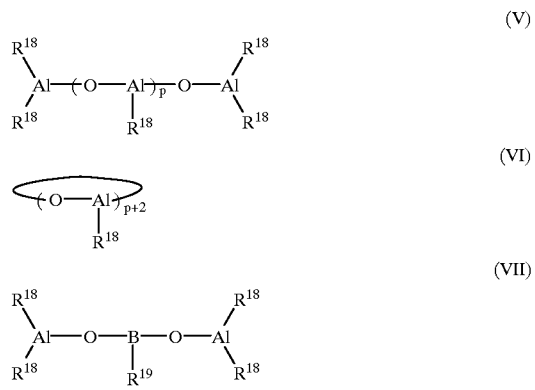

In the foregoing general formulae, $R^{18}$ represents a hydrogen atom or hydrocarbon residue, preferably a $C_{1-10}$, particularly $C_{1-6}$ hydrocarbon residue. The plurality of $R^{18}$'s may be the same or different. The suffix p represents an integer of from 0 to 40, preferably from 2 to 30.

The compound represented by the general formula (V) or (VI) is a compound also called alumoxane and can be obtained by reacting one or more trialkylaluminums with water. Specific examples of the compound represented by the general formula (V) or (VI) include (a) methyl alumoxane, ethyl alumoxane, propyl alumoxane, butyl alumoxane and isobutyl alumoxane, which are obtained from one trialkyl aluminum and water, and (b) methyl ethyl alumoxane, methyl butyl alumoxane and methyl isobutyl alumoxane, which are obtained from two trialkyl aluminums and water. Preferred among these compounds are methyl alumoxane and methyl isobutyl alumoxane.

A plurality of kinds of the foregoing alumoxanes may be used in each group and over groups. The foregoing alumoxane can be prepared under various known conditions. Specific examples of the preparation process will be given below.

(a) A process which comprises the direct reaction of a trialkyl aluminum with water in the presence of a proper organic solvent such as toluene, benzene and ether;

(b) A process which comprises the reaction of a trialkyl aluminum with a hydrous salt having water of crystallization such as hydrate of copper sulfate and aluminum sulfate;

(c) A process which comprises the reaction of a trialkyl aluminum with water content contained in silica gel;

(d) A process which comprises mixing a trimethyl aluminum and a triisobutyl aluminum, and then directly reacting the mixture with water in the presence of a proper organic solvent such as toluene, benzene and ether;

(e) A process which comprises the reaction of a mixture of a trimethyl aluminum and a triisobutyl aluminum with a hydrous salt having water of crystallization such as hydrate of copper sulfate and aluminum sulfate under heating;

(f) A process which comprises impregnating silica gel or the like with water content, and then treating the material thus impregnated with triisobutyl aluminum and then with a trimethyl aluminum;

(g) A process which comprises a synthesizing methyl alumoxane and isobutyl alumoxane by a known method, mixing the two components in a predetermined proportion, and then reacting the mixture under heating;

(h) A process which comprises allowing a salt having water of crystallization such as copper sulfate pentahydrate and trimethyl aluminum to undergo reaction in an aromatic hydrocarbon solvent such as benzene and toluene at a temperature of about −40° C. to 40° C.

The amount of water to be used in the reaction is normally from 0.5 to 1.5 mols per mol of trimethyl aluminum. The methyl alumoxane obtained by the foregoing method is a linear or cyclic organic aluminum polymer.

The compound represented by the foregoing general formula (VII) can be obtained by reacting one or more trialkyl aluminums with an alkylboric acid represented by the following general formula (VIII) in a proportion of 10:1 to 1:1 (by mol).

In the general formula (VIII), $R^{19}$ represents a $C_{1-10}$, preferably $C_{1-6}$ hydrocarbon residue or halogenated hydrocarbon group.

$$R^9B(OH)_2 \quad (VIII)$$

The following reaction products can be exemplified.

(a) 2:1 reaction product of trimethyl aluminum and methylboric acid;
(b) 2:1 reaction product of triisobutyl aluminum and methylboric acid;
(c) 1:1:1 reaction product of trimethyl aluminum, triisobutyl aluminum and methylboric acid;
(d) 2:1 reaction product of triethyl aluminum and ethylboric acid;
(e) 2:1 reaction product of trimethyl aluminum and butylboric acid An example of the ionic Compound capable of reaction with the component (A) to convert the component (A) to cation is a compound represented by the following general formula (IX):

$$[K]^{r+}[Z]^{r-} \quad (IX)$$

In the foregoing general formula (IX), K represents a cation component. Examples of the cation component include carbonium cation, tropylium cation, ammonium cation, oxonium cation, sulfonium cation, and phosphonium cation. Further examples of the cation component include cation of metals which can be easily reduced themselves and cation of organic metals.

Specific examples of the foregoing cations include triphenyl carbonium, diphenyl carbonium, cycloheptatrienium, indenium, triethyl ammonium, tripropyl ammonium, tributyl ammonium, N,N-dimethylanilium, dipropyl ammonium, dicyclohexyl ammonium, triphenyl phosphonium, trimethyl phosphonium, tris(dimethylphenyl) phosphonium, tris (methylphenyl) phosphonium, triphenyl sulfonium, triphenyl oxonium, triethyl oxonium, pyrilium, silver ion, gold ion, platinum ion, copper ion, palladium ion, mercury ion, and ferrocenium ion.

In the foregoing general formula (IX), Z represents an anion component which is a counter anion (normally non-coordination component) to the cation seed obtained by conversion of the component (A). Examples of Z include organic boron compound anion, organic aluminum compound anion, organic gallium compound anion, organic phosphor compound anion, organic arsenic compound anion, and organic antimony compound anion. Specific examples of these anions will be given below.

(a) Tetraphenylboron, tetrakis(3,4,5-trifluorophenyl) boron, tetrakis{3,5-bis(trifluoromethyl)phenyl} boron, tetrakis{3,5-di(t-butyl)phenyl} boron, tetrakis (pentafluorophenyl) boron, etc.;
(b) Tetraphenyl aluminum, tetrakis(3,4,5-trifluorophenyl) aluminum, tetrakis{3,5-bis(trifluoromethyl)phenyl} aluminum, tetrakis(3,5-di(t-butyl)phenyl) aluminum, tetrakis (pentafluorophenyl) aluminum, etc.;
(c) Tetraphenyl gallium, tetrakis(3,4,5-trifluorophenyl) gallium, tetrakis{3,5-bis(trifluoromethyl)phenyl} gallium, tetrakis{3,5-di(t-butyl)phenyl} gallium, tetrakis (pentafluorophenyl) gallium, etc.;
(d) Tetraphenyl phosphor, tetrakis(pentafluorophenyl) phosphor;
(e) Tetraphenyl arsenic, tetrakis(pentafluorophenyl) arsenic, etc.;
(f) Tetraphenyl antimony, tetrakis(pentafluorophenyl) antimony, etc.; and
(g) Decaborate, undecaborate, carbadodecaborate, decachlorodecaborate, etc.

As the Lewis acid, particularly Lewis acid capable of converting the component (A) to cation there may be exemplified various organic boron compounds, metal halide compounds, solid acids, etc. Specific examples of these compounds will be given below.

(a) Organic boron compound such as triphenyl boron, tris (3,5-difluorophenyl) boron and tris(pentafluorophenyl) boron;
(b) Metal halide compound such as aluminum chloride, aluminum bromide, aluminum iodide, magnesium chloride, magnesium bromide, magnesium iodide, magnesium bromochloride, magnesium chloroiodide, magnesium bromoiodide, magnesium chloride hydride, magnesium chloride hydroxide, magnesium bromide hydroxide, magnesium chloride alkoxide and magnesium bromide alkoxide; and
(c) Solid acid such as alumina and silica-alumina The particulate carrier as the optional component (C) to be incorporated in the catalyst for α-olefin polymerization of the present invention is one made of an inorganic or organic compound having a particle diameter of normally from 5 μm to 5 mm, preferably from 10 μm to 2 mm.

Examples of the foregoing carrier include oxides such as $SiO_2$, $Al_2O_3$, MgO, ZrO, $TiO_2$, $B_2O_3$ and ZnO, and composite oxides such as $SiO_2$—MgO, $SiO_2$—$Al_2O_3$, $SiO_2$—$TiO_2$, $SiO_2$—$Cr_2O_3$ and $SiO_2$—$Al_2O_3$—MgO.

Examples of the foregoing organic carrier include a particulate carrier of porous polymer made of (co)polymer of $C_{2-14}$ α-olefin such as ethylene, propylene, 1-butene and 4-methyl-1-pentene or (co)polymer of aromatic unsaturated hydrocarbon such as styrene and divinylbenzene. Such a particulate carrier normally has a specific surface area of from 20 to 1,000 m²/g, preferably from 50 to 700 m²/g, and a pore volume of not less than 0.1 cm²/g, preferably not less than 0.3 cm²/g, more preferably not less than 0.8 cm²/g.

The catalyst for α-olefin polymerization (1) of the present invention comprises as an optional component other than the particulate carrier an active hydrogen-containing compound such as $H_2O$, methanol and butanol, an electron donative compound such as ether, ester and amine or an alkoxy-containing compound such as phenyl phosphite, tetraethoxysilane and diphenyldimethoxysilane incorporated therein.

Other examples of the optional component include tri-lower alkyl aluminum such as trimethyl aluminum, triethyl aluminum and triisobutyl aluminum, halogen-containing alkyl aluminum such as diethyl aluminum chloride, diisobutyl aluminum chloride and methyl aluminum sesquichloride, alkyl aluminum hydride such as diethyl aluminum hydride, alkoxy-containing alkyl aluminum such as diethyl aluminum ethoxide and dimethyl aluminum butoxide, and aryloxy-containing alkyl aluminum such as diethyl aluminum phenoxide.

In the catalyst for α-olefin polymerization of the present invention, the aluminumoxy compound, the ionic compound capable of reacting the component (A) to convert the component (A) to cation and the Lewis acid are used singly as a component (B). Alternatively, these three components may be used in proper combination. Further, one or more of the foregoing lower alkyl aluminum, halogen-containing alkyl aluminum, alkyl aluminum hydride, alkoxy-containing alkyl aluminum and aryloxy-containing alkyl aluminum, though being optional components, are preferably incorporated in the catalyst for α-olefin polymerization in combination with the aluminumoxy compound, ionic compound or Lewis acid.

The catalyst (1) for α-olefin polymerization of the present invention can be prepared by allowing the foregoing components (A) and (B) to come in contact with each other in the presence or absence of the monomer to be polymerized inside or outside the polymerization tank. In some detail, the components (A) and (B) and optionally the component (C) may be separately introduced into the polymerization tank. Alternatively, the components (A) and (B) may be previously allowed to come in contact with each other before being introduced into the polymerization tank. Alternatively, the component (C) which has been impregnated with a mixture of the components (A) and (B) may be introduced into the polymerization tank.

The contact of these components may be effected in an inert gas such as nitrogen or an inert hydrocarbon solvent such as pentane, hexane, heptane, toluene and xylene. The temperature at which these components are allowed to come in contact with each other is preferably from –20° C. to the boiling point of the solvent used, particularly from room temperature to the boiling point of the solvent used. The catalyst thus prepared may or may not be washed before use. Further, the catalyst thus prepared may be used in combination with other components as necessary.

The previous contact of the components (A), (B) and (C) may involve so-called prepolymerization comprising the partial polymerization of α-olefin in the presence of monomers to be polymerized. In some detail, a prepolymerization product obtained by prepolymerizing an olefin such as ethylene, propylene, 1-butene, 1-hexene, 1-octene, 4-methyl-1-pentene, 3-methyl-1-butene, vinyl cycloalkane and styrene before polymerization, and then optionally washing the prepolymer may be used as a catalyst. This prepolymerization is preferably effected under mild conditions in an inert solvent such that a polymer is produced normally in an amount of from 0.01 to 1,000 g, preferably from 0.1 to 100 g per g of solid catalyst.

The amount of the components (A) and (B) to be used is arbitrary. For example, in the case of solvent polymerization, the amount of the component (A) to be used is normally from $10^{-7}$ to $10^2$ mmol/l, preferably from $10^{-4}$ to 1 mmol/l as calculated in terms of transition metal atom. In the case of aluminumoxy compound, the molar ratio of Al/transition metal is normally from 10 to $10^5$, preferably from 100 to $2 \times 10^4$, more preferably from 100 to $10^4$. On the other hand, the molar ratio of ionic compound or Lewis acid, if used as a component (B), to transition metal is normally from 0.1 to 1,000, preferably from 0.5 to 100, more preferably from 1 to 50.

The catalyst for α-olefin polymerization (2) of the present invention will be described hereinafter. This catalyst comprises an ion exchangeable layer compound excluding silicate or inorganic silicate incorporated therein as a component (D) and an organic aluminum compound incorporated therein as an optional component (E).

Examples of the foregoing ion exchangeable layer compound include ionic crystalline compounds of a hexagonal closest packing type, antimony type, $CdCl_2$ type or $CdI_2$ type, which have a layer crystal structure. Specific examples of such ion exchangeable layer compounds include crystalline salt of polyvalent metals such as α-$Zr(HAsO_4)_2 \cdot H_2O$, α-$Zr(HPO_4)_2$, α-$Zr(KPO_4)_2 \cdot 3H_2O$, α-$Ti(HPO_4)_2$, α-$Ti(HAsO_4)_2 \cdot H_2O$, α-$Sn(HPO_4)_2 \cdot H_2O$, γ-$Zr(HPO_4)_2$, γ-$Ti(HPO_4)_2$ and γ-$Ti(NH_4PO_4)_2 \cdot H_2O$.

The foregoing ion exchangeable layer compound may be optionally treated with a salt and/or acid before use. The ion exchangeable layer compound excluding silicate which is treated with neither salt nor acid has a crystal structure comprising a parallel laminate of planes made of ion bond or the like which are weakly bonded to each other. The ions contained in the ion exchangeable layer compound can be exchanged.

Examples of the foregoing inorganic silicate include clay, clay mineral, zeolite, and diatomaceous earth. These inorganic silicates may be in the form of synthetic product or naturally occurring mineral. Specific examples of clay and clay mineral include allophane group such as allophane, kaolin group such as dickite, nacrite, kaolinite and anauxite, halloysite group such as metahalloysite and halloysite, serpentine group such as chrysotile, lizardite and antigorite, smectite such as montmorillonite, sauconite, beidellite, nontronite, saponite and hectrite, vermiculite mineral such as vermiculite, mica mineral such as illite, sericite and glauconite, attapulgite, sepiolite, palygorskite, bentonite, kibushi clay, gairome clay, hisingerite, pyrophyllite, and chlorite group. These clays or clay minerals may form a mixture layer. Examples of the artificial synthetic products include synthetic mica, synthetic hectrite, synthetic saponite, and synthetic taeniolite.

Preferred among the foregoing inorganic silicates are kaolin group, halloysite group, serpentine group, smectite, vermiculite mineral, mica mineral, synthetic mica, synthetic hectrite, synthetic saponite, and synthetic taeniolite. Particularly preferred among these inorganic silicates are smectite, vermiculite mineral, synthetic mica, synthetic hectrite, synthetic saponite, and synthetic taeniolite. These inorganic silicates may be used untreated or after treatment by ball mill, sifting, etc. These inorganic silicates may be used singly or in admixture.

The foregoing inorganic silicate may be optionally subjected to treatment with a salt and/or acid to change the solid acid strength. The treatment with a salt may be effected such that an ion complex, molecular complex, organic derivative, etc. is formed, making it possible to change the surface area or interlayer distance of the inorganic silicate. In some detail, exchangeable ions between layers can be exchanged with other bulky ions by making the use of ion exchangeability to obtain a layer substance having a raised interlayer distance.

The ion exchangeable layer compound and the inorganic silicate may be used untreated. In practice, however, the exchangeable metal cations contained in these compounds are preferably exchanged with cations separated from the following salt and/or acid.

The foregoing salt to be used in ion exchange is a compound containing cations comprising at least one atom selected from the group consisting of atoms belonging to the groups 1 to 14, preferably a compound made of cations comprising at least one atom selected from the group consisting of atoms belonging to the groups 1 to 14 and anions derived from at least one atom or atomic group selected from the group consisting of halogen atom, inorganic acid and organic acid, more preferably a compound made of cations comprising at least one atom selected from the group consisting of atoms belonging to the groups 2 to 14 and at least one anion selected from the group consisting of Cl, Br, I, F, $PO_4$, $SO_4$, $NO_3$, $CO_3$, $C_2O_4$, $ClO_4$, $OOCCH_3$, $CH_3COCHCOCH_3$, $OCl_2$, $O(NO_3)_2$, $O(ClO_4)_2$, $O(SO_4)$, OH, $O_2Cl_2$, $OCl_3$, OOCH and $OOCCH_2CH_3$. Two or more of these salts may be used in combination.

The foregoing acid to be used in ion exchange is preferably selected from the group consisting of hydrochloric acid, sulfuric acid, nitric acid, acetic acid and oxalic acid. Two or more of these acids may be used in combination. Examples of the process involving treatment with a salt and treatment with an acid include a process which comprises treatment with a salt followed by treatment with an acid, a process which comprises treatment with an acid followed by treatment with a salt, a process which comprises effecting treatment with a salt and treatment with an acid at the same time, and a process which comprises treatment with a salt followed by the simultaneous execution of treatment with a salt and treatment with an acid. The treatment with an acid has an effect of exchanging ions and removing surface impurities as well as eluting some cations such as Al, Fe, Mg and Li ions from the crystal structure.

The conditions under which treatment with a salt and treatment with an acid are effected are not specifically limited. In practice, however, these treatments are preferably effected with a salt and an acid each in a concentration of from 0.1 to 30% by weight at a temperature of from room temperature to the boiling point of the solvent used for from 5 minutes to 24 hours under conditions such that the compound to be treated is partially eluted. The salt and acid are normally used in the form of aqueous solution.

The foregoing treatment with a salt and/or acid, if effected, may be preceded, accompanied or followed by grinding or granulation to control the shape of the compound to be treated. Alternatively, other chemical treatments such as treatment with an alkali, organic compound and organic metal compound may be effected as well. The component (D) thus obtained preferably has pores having a radius of not less than 20 Å as determined by mercury penetration method in a volume proportion of not less than 0.1 cc/g, particularly from 0.3 to 5 cc/g. Such a component (D), if treated in an aqueous solution, contains adsorbed water and interlayer water. The term "adsorbed water" as used herein is meant to indicate water adsorbed by the surface of the ion exchangeable layer compound or inorganic silicate or the fractured surface of crystal. The term "interlayer water" as used herein is meant to indicate water present between layers of the crystal.

In the present invention, the component (D) is preferably freed of such an adsorbed water and interlayer water before use. The process for the removal of such an adsorbed water and interlayer water is not specifically limited. In practice, however, dehydrated under heating, dehydrated under heating in a gas flow, dehydration under heating and reduced pressure or dehydration under azeotropy with an organic solvent may be used. The heating temperature is such that adsorbed water and interlayer water are not left behind. It is normally not lower than 100° C., preferably not lower than 150° C. However, it should not be so high as to cause structural failure. The heating time is not less than 0.5 hours, preferably not less than 1 hour. The weight loss of the component (D) after dehydration is preferably not more than 3% by weight if is subjected to suction at a temperature of 200° C. under a pressure of 1 mmHg for 2 hours. In the present invention, if a component (D) the weight loss of which has been adjusted to not more than 3% by weight is used, it is preferably kept in the same conditions during contact with the component (A) and the following optional component (E).

An example of the organic aluminum compound to be incorporated as an optional component (E) in the catalyst for α-olefin polymerization (2) of the present invention is represented by the following general formula (X):

$$AlR_aP_{3-a} \qquad (X)$$

In the foregoing general formula (X), R represents a $C_{1-20}$ hydrocarbon group, P represents a hydrogen atom, halogen atom, alkoxy group or siloxy group, and the suffix a represents a number of from more than 0 to not more than 3. Specific examples of the organic aluminum compound represented by the general formula (X) include trialkyl aluminum such as trimethyl aluminum, triethyl aluminum, tripropyl aluminum and triisobutyl aluminum, and halogen- or alkoxy-containing alkyl aluminum such as diethyl aluminum monochloride and diethyl aluminum monomethoxide. Preferred among these organic aluminum compounds is trialkyl aluminum. As the component (E) to be incorporated in the catalyst for α-olefin polymerization (2) of the present invention there may be used an aluminoxane such as methyl aluminoxane other the organic aluminum compound represented by the general formula (X). The organic aluminum compound and aluminoxane may be used in combination.

The catalyst for α-olefin polymerization (2) of the present invention can be prepared in the same manner as for the catalyst for α-olefin polymerization (1) of the present invention. The process for the contact of the components (A) and (D) with the optional component (E) is not specifically limited. In practice, however, the following processes may be exemplified. This catalytic process may be effected not only during the preparation of catalyst but also during the prepolymerization by olefin or olefin polymerization.

(1) Process involving the contact of the component (A) with the component (D);
(2) Process involving the contact of the component (A) with the component (D) followed by the addition of the component (E);
(3) Process involving the contact of the component (A) with the component (E) followed by the addition of the component (D);
(4) Process involving the contact of the component (D) with the component (E) followed by the addition of the component (A); and
(5) Process involving the simultaneous contact of the components (A), (D) and (E)

The contact of the foregoing various components may be accompanied or followed by the presence or contact of a polymer such as polyethylene and polypropylene or an inorganic solid oxide such as silica and alumina.

The contact of the foregoing various components may be effected in an inert gas such as nitrogen and an inert hydrocarbon solvent such as pentane, hexane, heptane, toluene and xylene. The contact of these components is effected preferably at a temperature of from −20° C. to the boiling point of the solvent used, particularly from room temperature to the boiling point of the solvent used.

The amount of the foregoing various components to be used are as follows. In some detail, the amount of the component (A) and the component (E) to be used per g of the component (D) are normally from $10^{-4}$ to 10 mmol and from 0.01 to $10^4$ mmol, preferably from $10^{-3}$ to 5 mmol and from 0.1 to 100 mmol, respectively. The atomic ratio of transition metal in the component (A) to aluminum in the component (E) is normally from 1:0.01 to $10^6$, preferably from 1:0.1 to $10^5$. The catalyst thus prepared may or may not be washed before use. The catalyst thus prepared may be used in combination with another component (E) as necessary. In other words, if the components (A) and/or (D) and the component (E) are used to prepare a catalyst, the component (E) may be further added to the reaction system separately from the preparation of catalyst. The amount of the component (E) to be used herein is predetermined to be from 1:0 to $10^4$, preferably from 1:1 to $10^3$ as calculated in terms of atomic ratio of aluminum in the component (E) to transition metal in the component (A).

The process for the preparation of the α-olefin polymer of the present invention will be further described hereinafter. In the present invention, the foregoing catalyst of the present invention and an α-olefin are allowed to come in contact with each other to cause polymerization or copolymerization. The catalyst for α-olefin polymerization (1) or (2) of the present invention can be applied to solvent polymerization using solvent as well as to liquid phase solvent-free polymerization substantially free from solvent, gas phase polymerization and melt polymerization. The polymerization process may be effected in either continuous or batch-wise process.

As the solvent to be used in solvent polymerization there may be used an inert saturated aliphatic or aromatic hydrocarbon such as hexane, heptane, pentane, cyclohexane, benzene and toluene, singly or in admixture. The polymerization temperature is normally from −78° C. to 250° C., preferably from −20° C. to 100° C. The olefin pressure in the reaction system is not specifically. limited but is preferably from atmospheric pressure to 2,000 kgf/cm$^2$G, more preferably from atmospheric pressure to 50 kgf/cm$^2$G. Further, the molecular weight of the resulting polymer can be properly adjusted by any known method such as predetermination of temperature or pressure and introduction of hydrogen.

As the α-olefin to be used as a starting material there may be used a $C_{2-20}$, preferably $C_{2-10}$ α-olefin. Specific examples of such an α-olefin include ethylene, propylene, 1-butene, 4-methyl-1-pentene, 1-hexene, 1-octene, 1-decene, 1-dodecene, 1-tetradecene, 1-hexadecene, 1-octadecene, and 1-eicosene. The catalyst of the present invention may be preferably used in the polymerization of a $C_{3-10}$ α-olefin, particularly propylene, for the purpose of stereoregular polymerization.

The catalyst of the present invention can also be applied to the copolymerization of the foregoing various α-olefins with each other or with other monomers. Examples of the other monomers copolymerizable with α-olefin include conjugated or nonconjugated dienes such as butadiene, 1,4-hexadiene, 1,5-hexadiene, 7-methyl-1,6-octadiene, 1,8-nonadiene and 1,9-decadiene, and cyclic olefins such as cyclopropene, cyclobutene, cyclopentene, norbornene and dicyclopetandiene. The polymerization of these olefins may be accomplished by so-called multi-stage polymerization involving the change of conditions by stages, e.g., so-called block copolymerization involving polymerization at the first stage and subsequent copolymerization of ethylene with propylene at the second stage.

The use of the transition metal compound of the present invention as a catalyst component for α-olefin polymerization makes it possible to exert some effects as described in the following examples. For example, the polymer thus obtained has a raised melting point, a raised molecular weight and a reduced MFR. The reason for this effect is not necessarily obvious but can be presumed as follows after a fashion.

In other words, the substituents $R^7$ and/or $R^8$ in the transition metal compound of the present invention are sterically configured to make some angle from the plane of a condensed ring formed by the 5-membered ring moiety thereof and $R^3$ and/or $R^6$ to which they are connected because $R^3$ and/or $R^6$ forms a condensed ring consisting of 7 or more members. Further, the substituents $R^7$ and/or $R^8$ comprises an oxygen-containing aryl group, nitrogen-containing aryl group or sulfur-containing aryl group which is sterically bulkier than hydrogen atom. Such an aryl group forms a proper steric hindrance and shape which cannot be realized by hydrocarbon alone. As a result, the action of regulating the direction of growth of polymer chain and the orientation direction of monomer can be enhanced. The resulting polymer exhibits an enhanced stereoregularity that raises the melting point thereof.

It can further be presumed that the electronic action of oxygen atom, nitrogen atom or sulfur atom on the central metal (e.g., zirconium, hafnium) and the foregoing steric structure make it possible to inhibit chain transfer reaction and hence provide a polymer having an increased molecular weight.

EXAMPLES

The present invention will be further described in the following examples, but the present invention should not be construed as being limited thereto. In the following examples, the process for the synthesis of catalyst and the polymerization process were effected all in an atmosphere of purified nitrogen. The solvent used had been dehydrated by MS-4A, and then deaerated by bubbling purified nitrogen thereinto. The activity per unit solid catalyst component is represented by catalyst activity (unit: g polymer/g solid). The activity per unit complex component is represented by complex activity (unit: g polymer/g complex).

(1) Measurement of MFR

To 6 g of the polymer was added 6 g of a 0.6 wt-% acetone solution of a heat stabilizer (BHT). Subsequently, the foregoing polymer was dried, packed into a melt indexer (230° C.), and then allowed to stand under a load of 2.16 kg. Thereafter, the amount of the polymer thus extruded was measured. The measurements were then converted to amount per 10 minutes to determine MFR.

(2) Measurement of Molecular Weight Distribution

The molecular weight distribution was determined by the ratio of weight-average molecular weight (Mw) to number-average molecular weight (Mn) (Mw/Mn=Q) as measured by GPC. As GPC apparatus there was used a Type 150CV GPC apparatus produced by Waters Inc. The measurement was effected at a temperature of 135° C.

(3) Measurement of Melting Point

For the measurement of melting point, a Type TA2000 DSC produced by Du Pont Inc. was used. The specimen was once heated and cooled at a rate of 10° C./min. between 20° C. and 200° C. The measurement of melting point was effected during the second temperature rise.

Example 1

(1) Synthesis of dichloro{1,1'-dimethylsilylenebis [2-methyl-4-(6-methoxy-2-naphthyl)-4H-azulenyl]}hafnium (a) Synthesis of racemic-meso mixture of dichloro{1,1'-dimethylsilylenebis[2-methyl-4-(6-methoxy-2-naphthyl)-4H-azulenyl]}hafnium 2.37 g of 2-bromo-6-methoxynaphthalene was dissolved in a mixture of 80 ml of diethyl ether and 80 ml of n-hexane, and then cooled to a temperature of −65° C. During the procedure, the solute was precipitated to obtain a white suspension. To the suspension was then added dropwise 12.3 ml of t-butyl lithium (1.62 M pentane solution) at a temperature of from −65° C. to −60° C. The mixture was then stirred at a temperature of −70° C. for 30 minutes. The temperature of the mixture was then gradually raised to −15° C. where the mixture was then stirred for 90 minutes. At a temperature of −10° C., to the mixture was then added 1.41 g of 2-methylazulene. The cooling bath was then removed. The mixture was then stirred at room temperature for 2 hours. The reaction solution was then again cooled to a temperature of 4° C. To the reaction mixture were then added dropwise sequentially 80 ml of tetrahydrofuran, 0.012 ml of N-methylimidazole and 0.64 g of dimethylsilyl dichloride. The reaction mixture was then stirred for 30 minutes. The reaction temperature of the reaction solution was then gradually raised to room temperature where it was then stirred for 1 hour. To the reaction solution was then added 50 ml of a 1 N aqueous solution of hydrochloric acid. The reaction solution was extracted with diethyl ether, and then dried over magnesium sulfate. The resulting organic phase was then concentrated under reduced pressure. The amorphous solid (ligand) thus obtained was not then further purified before being used in the subsequent reaction.

3.50 g of the amorphous solid thus obtained was dissolved in 50 ml of diethyl ether, and then cooled to a temperature of −70° C. To the mixture was then added dropwise 6.2 ml of n-butyl lithium (1.61 M n-hexane solution). The reaction mixture was then stirred at the same temperature for 10 minutes. The temperature of the reaction solution was then gradually raised to room temperature where the reaction solution was then stirred for 2 hours. The solvent was then distilled off under reduced pressure. To the residue were then added 100 ml of toluene and 5 ml of diethyl ether. The reaction mixture was then cooled to a temperature of −70° C. To the reaction mixture was then added 1.60 g of hafnium tetrachloride. The reaction mixture was then stirred at a temperature of −70° C. for 10 minutes. The temperature of the reaction solution was then gradually raised to room temperature where the reaction solution was then stirred for 60 hours. The reaction solution was then concentrated under reduced pressure to make about 40 ml. The residue was then filtered through Celite. The solid on the Celite filter was then washed with 40 ml of toluene. The solid was then extracted with 60 ml of methylene chloride from the Celite filter. The resulting bright brown transparent filtrate was concentrated, and then dried to obtain 0.32 g of the titled racemic-meso mixture in the form of yellow white powder.

(b) Purification of Racemate 82 mg of the foregoing racemic-meso mixture was dissolved in 50 ml of methylene chloride, and then introduced into a pyrex vessel equipped with a 100 W high pressure mercury vapor lamp. The solution was then irradiated with light (300 nm to 600 nm) with stirring at atmospheric pressure for 5 minutes so that the proportion of racemate was enhanced. Methylene chloride was then distilled off under reduced pressure. To the residue was then added 15 ml of toluene. The mixture was then stirred to form a suspension. The solid was then withdrawn by filtration through a Celite filter. The solid on the Celite filter was washed with 5 ml of toluene five times and with 5 ml of hexane three times, and then extracted with 30 ml of methylene chloride. Methylene chloride was then distilled off under reduced pressure to obtain 26 mg of a racemate of dichloro{1,1'-dimethylsilylenebis[2-methyl-4-(6-methoxy-2-naphthyl)-4H-azulenyl]}hafnium.

The chemical shift in $^1$H-NMR of the foregoing racemate was as follows: 300 MHz, $C_6D_6$ (ppm): 1.01 (6H, s, $SiMe_2$), 2.25 (6H, s, 2-Me), 3.93 (6H, s, OMe), 5.2 (2H, m, 4-H), 5.8–6.3 (6H, m), 6.8–7.8 (16H, m)

(2) Polymerization of propylene in the presence of methyl alumoxane as a co-catalyst Into an agitated autoclave having an inner volume of 2 l was charged 4 mmol (as calculated in terms of aluminum atom) of methyl alumoxane (MMAO, produced by TOSOH AKZO CORP.). Separately, into a catalyst feeder with an explosion disc was introduced 0.36 mg of the foregoing racemate which had been diluted with toluene. Thereafter, into the autoclave was charged 1,400 ml of propylene. The explosion disc was then cut at room temperature. The temperature of the reaction mixture was then raised to 70° C. where the reaction mixture was then subjected to polymerization for 1 hour to obtain 13.0 g of a polypropylene. The complex activity was $3.6 \times 10^4$. The polypropylene thus obtained exhibited Tm of 155.7° C., MFR of 0.04, Mw of $7.2 \times 10^5$ and Q of 3.1.

Example 2

Polymerization of Propylene in the Presence of Clay Mineral as a Co-catalyst (1) Chemical treatment of clay mineral and preparation of solid catalyst component 10 g of montmorillonite ("Kunipia F", produced by Kunimine Industry Corp.) was dispersed in a diluted sulfuric acid comprising 10 g of sulfuric acid and 90 ml of desalted water. The dispersion was heated to the boiling point thereof, and then stirred for 6 hours. Thereafter, montmorillonite thus recovered was thoroughly washed with desalted water, predried, and then dried at a temperature of 200° C. for 2 hours to obtain a chemically treated clay mineral.

To 200 mg of the chemically treated montmorillonite was then added 1.0 ml of a 0.4 mol/l toluene solution of triethyl aluminum. The mixture was then stirred at room temperature for 1 hour. The reaction solution was then washed with toluene to obtain a 33 mg/ml toluene slurry of clay mineral.

(2) Polymerization of Propylene

Into an agitated autoclave having an inner volume of 1 l was charged 0.25 mmol (as calculated in terms of aluminum atom) of triisobutyl aluminum (produced by TOSOH AKZO CORP.). Separately, into a catalyst feeder with an explosion disc was introduced 1.36 mg of the foregoing racemate obtained in Example 1 (1) which had been diluted with toluene. Into the catalyst feeder were then introduced the toluene slurry of 50 mg of montmorillonite prepared in the process (1) and 0.015 mmol (as calculated in terms of aluminum atom) of triisobutyl aluminum. Thereafter, into the autoclave was introduced 700 ml of propylene. The explosion disc was then cut at room temperature. The temperature of the reaction solution was then raised to 80° C. where the reaction solution was then subjected to polymerization for 1 hour to obtain 69.2 g of a polypropylene. The catalyst activity and complex activity were 1,380 and $5.1 \times 10^4$, respectively. The polypropylene thus obtained exhibited Tm of 153.1° C., MFR of 0.6, Mw of $5.3 \times 10^5$ and Q of 3.2.

Example 3

(1) Synthesis of dichloro{1,1'-dimethylsilylenebis [2-methyl-4-(6-t-butyldimethylsiloxy-2-naphthyl)-4H-azulenyl]}hafnium (a) Synthesis of 2-bromo-6-t-butyldimethylsilyloxy naphthalene 3.0 g of 2-bromo-6-naphthol and 1.75 g of imidazole were dissolved in 30 ml of dimethylforamide. To the solution was then added 2.33 g of t-butyldimethylsilyl dichloride at a temperature of 0° C. The reaction solution was stirred at a temperature of 0° C. for 2 hours and then at room temperature overnight. The reaction solution was poured into saturated brine, and then extracted with diethyl ether. The resulting organic phase was then dried over sodium sulfate. The organic phase was then concentrated under reduced pressure. The residue was then purified through silica gel column chromatography to obtain 4.36 g of the titled compound in the form of white solid.

The chemical shift in $^1$H-NMR of the titled compound was as follows: 300 MHz, $CDCl_3$ (ppm): 0.24 (6H, s), 1.00 (9H, s), 7.09 (1H, dd, J=2.4 Hz, 9.0 Hz), 7.15 (1H, d, J=2.4 Hz), 7.47 (1H, dd, J=1.8 Hz, 8.7 Hz), 7.56 (1H, d. J=8.7 Hz), 7.63 (1H, d, J=8.7 Hz), 7.91 (1H, d. J=1.8 Hz)

(b) Synthesis of racemic-meso mixture of dichloro{1,1'-dimethylsilylenebis[2-methyl-4-(6-t-butyldimethylsiloxy-2-naphthyl)-4H-azulenyl]} hafnium 3.86 g 2-bromo-6-t-butyldimethylsilyloxy naphthalene obtained in the process (a) was dissolved in a mixture of 35 ml of diethyl ether and 35 ml of n-hexane, and then cooled to a temperature of −70° C. During the procedure, the solute was precipitated to obtain a white suspension. To the suspension was then added dropwise 14.1 ml of t-butyl lithium (1.62 M pentane solution) at a temperature of from −70° C. to −65° C. The mixture was then stirred at a temperature of −70° C. for 15 minutes. The temperature of the mixture was then gradually raised to 0° C. where the mixture was then stirred for 100 minutes. At a temperature of −2° C., to the mixture was then added 1.545 g of 2-methylazulene. The reaction mixture was then stirred at the same temperature for 5 minutes. The temperature of the reaction solution was then gradually raised to room temperature where the reaction solution was then stirred for 1 hour. The reaction solution was then again cooled to a temperature of 0° C. To the reaction solution was then added dropwise sequentially 35 ml of tetrahydrofuran, 0.013 ml of N-methylimidazole and 0.70 g of dimethylsilyl dichloride. The reaction mixture was then stirred for 30 minutes. The reaction temperature of the reaction solution was then gradually raised to room temperature where it was then stirred for 1.5 hours. The reaction solution was poured into saturated aqueous solution of ammonium chloride, and then extracted with diethyl ether. The resulting organic phase was washed with saturated brine, and then dried over magnesium sulfate. The resulting organic phase was then concentrated under reduced pressure. The amorphous solid (ligand) thus obtained was not then further purified before being used in the subsequent reaction.

5.434 g of the amorphous solid thus obtained was dissolved in 60 ml of diethyl ether, and then cooled to a temperature of −70° C. To the mixture was then added dropwise 6.8 ml of n-butyl lithium (1.61 M n-hexane solution). The reaction mixture was then stirred at the same temperature for 15 minutes. The temperature of the reaction solution was then gradually raised to room temperature where the reaction solution was then stirred for 3.5 hours. The solvent was then distilled off under reduced pressure. To the residue were then added 130 ml of toluene and 6 ml of diethyl ether. The reaction mixture was then cooled to a temperature of −70° C. To the reaction mixture was then added 1.74 g of hafnium tetrachloride. The reaction mixture was then stirred at a temperature of −70° C. for 15 minutes. The temperature of the reaction solution was then gradually raised to room temperature where the reaction solution was then stirred overnight. The reaction solution was then concentrated under reduced pressure to reduce the amount thereof to about ⅓. The residue was then filtered through Celite. The solid on the Celite filter was then washed with 15 ml of toluene. The resulting dark brown filtrate was then concentrated and dried. To the filtrate was then added 12 ml of n-hexane. The reaction mixture was then stirred and allowed to stand to cause sedimentation of a Chinese yellow powder. The powder thus sedimented was withdrawn by filtration through Celite, washed with 15 ml of hexane, and then eluted with 30 ml of methylene chloride. Methylene chloride was then distilled off under reduced pressure to obtain 1.30 g of the titled racemic-meso mixture in the form of yellow solid.

The chemical shift in $^1$H-NMR of the titled racemic-meso mixture was as follows: 300 MHz, $C_6D_6$ (ppm): 0.13 (6H, s, meso-$SiMe_2$), 0.15 (12H, s, racemic-$SiMe_2$), 0.16 (6H, s, meso-$SiMe_2$), 0.45 (3H, s, meso-$SiMe_2$), 0.53 (6H, s, racemic-$SiMe_2$), 0.61 (3H, s, meso-$SiMe_2$), 1.02–1.03 (18H, Sit-Bu), 1.93 (6H, s, meso-2-Me), 2.02 (6H, s, racemic-2-Me), 5.57 (2H, m, racemic-4-H), 5.65 (2H, m, meso-4-H), 5.8–6.1 (6H+2H, m), 6.13 (2H, s, racemic-3-H), 6.75 (2H, d, J=11 Hz, racemic-Ar), 6.9 (2H, d, J=11 Hz, meso-Ar), 7.0–7.1 (2H, m), 7.24 (2H, d, J=2.4 Hz, meso-Ar), 7.27 (2H, d, J=2.4 Hz, racemic-Ar), 7.52–7.6 (4H, m), 7.7–7.8 (2H, m), 7.9 (2H, s)

(c) Purification of Racemate 190 mg of the foregoing racemic-meso mixture was dissolved in 20 ml of benzene, and then introduced into a pyrex vessel equipped with a 100 W high pressure mercury vapor lamp. The solution was then irradiated with light (300 nm to 600 nm) with stirring at atmospheric pressure for 10 minutes so that the proportion of racemate was enhanced. Benzene was then distilled off under reduced pressure. To the residue was then added 7.5 ml of n-hexane. The mixture was stirred, and then allowed to stand to cause sedimentation of a light yellow solid. The resulting supernatant liquid was then removed. To the residue was then added 7.5 ml of n-hexane. The mixture was then stirred. The solid was then withdrawn by filtration through a Celite filter. The solid on the Celite filter was washed with 3 ml of a 5:1 mixture of n-hexane and benzene three times, and then extracted with methylene chloride. Methylene chloride was then distilled off under reduced pressure to obtain 62 mg of a racemate of dichloro{1,1'-dimethylsilylenebis[2-methyl-4-(6-t-butyldimethylsiloxy-2-naphthyl)-4H-azulenyl]}hafnium.

The chemical shift in $^1$H-NMR of the foregoing racemate was as follows: 300 MHz, $C_6D_6$ (ppm): 0.15 (12H, s, $SiMe_2$), 0.53 (6H, s, $SiMe_2$), 1.03 (18H, Sit-Bu), 2.02 (6H, s, 2-Me), 5.57 (2H, m, 4-H), 5.75–6.05 (6H, m), 6.13 (2H, s, 3-H), 6.75 (2H, d, J=11 Hz), 6.13 (2H, s, 3-H), 6.75 (2H, d, J=11 Hz), 7.05 (2H, dd, J=9 Hz, 2.4 Hz), 7.27 (2H, d, J=2.4 Hz), 7.54 (2H, d, J=9 Hz), 7.59 (2H, d, J=8.4 Hz), 7.71 (2H, dd, J=8.4 Hz, 1.8 Hz), 7.9 (2H, d, J=1.0 Hz)

(2) Polymerization of Propylene in the Presence of Methyl Alumoxane as a Co-catalyst Into an agitated autoclave having an inner volume of 1 l was charged 4 mmol (as calculated in terms of aluminum atom) of methyl alumoxane (MMAO, produced by TOSOH AKZO CORP.). Separately, into a catalyst feeder with an explosion disc was introduced 0.44 mg of the foregoing racemate which had been diluted with toluene. Thereafter, into the autoclave was charged 700 ml of propylene. The explosion disc was then cut at room temperature. The temperature of the reaction mixture was then raised to 70° C. where the reaction mixture was then subjected to polymerization for 1 hour to obtain 90.0 g of a polypropylene. The complex activity was 20.4×10$^4$. The polypropylene thus obtained exhibited Tm of 155.0° C., MFR of 0.05, Mw of 9.2×10$^5$ and Q of 3.6.

Example 4

Polymerization of Propylene in the Presence of Clay Mineral as a Co-catalyst

Into an agitated autoclave having an inner volume of 1 l was charged 0.25 mmol (as calculated in terms of aluminum atom) of triisobutyl aluminum (produced by TOSOH AKZO CORP.). Separately, into a catalyst feeder with an explosion disc was introduced 1.66 mg of the foregoing racemate obtained in Example 3 (1) which had been diluted with toluene. Into the catalyst feeder were then introduced the toluene slurry of 50 mg of montmorillonite prepared in the same manner as in Example 2 (1) and 0.015 mmol (as calculated in terms of aluminum atom) of triisobutyl aluminum. Thereafter, into the autoclave was introduced 700 ml of propylene. The explosion disc was then cut at room temperature. The temperature of the reaction solution was then raised to 80° C. where the reaction solution was then subjected to polymerization for 1 hour to obtain 123.6 g of a polypropylene. The catalyst activity and complex activity were 2,470 and 7.5×10$^4$, respectively. The polypropylene thus obtained exhibited Tm of 154.6° C., MFR of 0.26, Mw of 6.4×10$^5$ and Q of 2.8.

Example 5

(1) Synthesis of dichloro{1,1'-dimethylsilylenebis [2-methyl-4-(4-phenoxyphenyl)-4H-azulenyl]} hafnium 6.0 g of 4-phenoxyphenyl bromide was dissolved in a mixture of 5 ml of diethyl ether and 60 ml of n-hexane, and then cooled to a temperature of −70° C. To the solution was then added dropwise 30.3 ml of t-butyl lithium (1.59 M pentane solution) at a temperature of from −70° C. to −65° C. The mixture was then stirred at a temperature of −70° C. for 15 minutes. The temperature of the mixture was then gradually raised to −10° C. where 3.08 g of 2-methylazlen was added thereto. The cooling bath was then immediately removed. The temperature of the reaction solution was then raised to room temperature where the reaction solution was then stirred for 1 hour. The reaction solution was then again cooled to a temperature of 0° C. To the reaction mixture were then added dropwise sequentially 40 ml of tetrahydrofuran, 0.04 ml of N-methylimidazole and 1.40 g of dimethylsilyl dichloride. The reaction mixture was then stirred for 10 minutes. The reaction temperature of the reaction solution was then gradually raised to room temperature where it was then stirred for 1.5 hours. The reaction solution was poured into saturated aqueous solution of ammonium chloride, and then extracted with diethyl ether. The resulting organic phase was washed with saturated brine, and then dried over magnesium sulfate. The resulting organic phase was then concentrated under reduced pressure. The amorphous solid (ligand) thus obtained was not then further purified before being used in the subsequent reaction.

The amorphous solid thus obtained was dissolved in 35 ml of diethyl ether, and then cooled to a temperature of −70° C. To the mixture was then added dropwise 13.5 ml of n-butyl lithium (1.61 M n-hexane solution). The reaction mixture was then stirred at the same temperature for 20 minutes. The temperature of the reaction solution was then gradually raised to room temperature where the reaction solution was then stirred for 2 hours. To the reaction mixture was then added 240 ml of toluene. The reaction mixture was then cooled to a temperature of −70° C. To the reaction mixture was then added 3.2 g of hafnium tetrachloride. The reaction mixture was then stirred at a temperature of −70° C. for 20 minutes. The temperature of the reaction solution was then gradually raised to room temperature where the reaction solution was then stirred overnight. The reaction solution was then concentrated under reduced pressure to make about 40 ml. The residue was then filtered through Celite. The resulting dark brown filtrate was then concentrated and dried. The residue was then dissolved in 15 ml of methylene chloride. To the solution was then added 15 ml of n-hexane. The reaction solution was stirred, and then allowed to stand to cause sedimentation of a Chinese yellow powder. The resulting supernatant liquid was then removed. The powder thus obtained was then dried under reduced pressure to obtain 1.40 g of the titled racemic-meso mixture in the form of light brown solid.

The chemical shift in $^1$H-NMR of the titled racemic-meso mixture was as follows: 300 MHz, CDCl$_3$ (ppm): 1.0 (6H, SiMe$_2$), 2.29 (6H, s, racemic-2-Me), 2.3 (6H, s, meso-2-Me), 5.01 (2H, d, J=4 Hz, racemic-4-H), 5.08 (2H, d, J=4 Hz, meso-4-H), 5.8–6.15 (6H+2H, m), 5.89 (2H, s, racemic-3-H), 6.8–7.5 (20H, m)

Example 6

Polymerization of Propylene in the Presence of Clay Mineral as a Co-catalyst

The procedure of Example 4 was followed except that 4.6 mg of the racemic-meso mixture synthesized in Example 5 (1) was used instead of the racemate synthesized in Example 3 (1). Thus, 105.7 g of a polypropylene was obtained. The catalyst activity and complex activity were 2,110 and 2.3×10$^4$, respectively. The polypropylene thus obtained exhibited Tm of 152.4° C. and MFR of 0.60.

Comparative Example 1

The polymerization procedure of Example 1 (2) was followed except that 0.298 mg of a racemate of dichloro[1, 1'-dimethylsilylenebis(2-methyl-4-phenyl)-4H-azulenyl] hafnium synthesized in the same manner as in Example 1 (1) was used instead of dichloro{1,1'-dimethylsilylenebis[2-methyl-4-(6-methoxy-2-naphthyl)-4H-azulenyl]}hafnium. Thus, 32 g of a polypropylene was obtained. The complex activity was 10.7×10$^4$. The polypropylene thus obtained exhibited Tm of 154.4° C., MFR of 0.08, Mw of 8.4×10$^5$ and Q of 3.8.

Comparative Example 2

The polymerization procedure of Example 4 was followed except that 1.12 mg of a racemate of dichloro[1,1'-dimethylsilylenebis(2-methyl-4-phenyl)-4H-azulenyl] hafnium was polymerized for 35 minutes instead of dichloro{1,1'-dimethylsilylenebis[2-methyl-4-(6-t-butyldimethylsiloxy-2-naphthyl) -4H-azulenyl]}hafnium. Thus, 163 g of a polypropylene was obtained. The catalyst activity and complex activity were 3,260 and 25.0×10$^4$, respectively. The polypropylene thus obtained exhibited Tm of 152.7° C., MFR of 0.8, Mw of 4.1×10$^5$ and Q of 2.6.

Comparative Example 3

(1) Chemical Treatment of Clay Minerals and Preparation of Solid Catalyst Component 10 g of montmorillonite ("KUNIPIA F" produced by KUNIMINE INDUSTRIES CO., LTD.) was dispersed in dilute sulfuric acid composed of 10 g of sulfuric acid and 90 ml of desalted water. The resultant dispersion was heated up to a boiling point thereof, followed by stirring at that temperature for 6 hours. Thereafter, the montmorillonite recovered was sufficiently washed with desalted water and, after pre-drying, dried at 200° C. for 2 hours to obtain a chemically treated clay minerals. 200 mg of the chemically treated montmorillonite was added to 0.8 ml of a toluene solution of tritehylaluminum (0.5 mol/liter). The mixture was stirred at room temperature for one hour, and then washed with toluene to obtain a montmorillonite/toluene slurry containing montmorillonite in an amount of 20 mg/ml.

(2) Polymerization of Propylene 0.45 mmol of triethylaluminum, a slurry of chemically treated clay minerals described hereinafter in the above item (1) and 700 ml of liquid propylene were charged into a 1-liter stirring-type autoclave at room temperature in the presence of a nitrogen streatm. Further, 1.5 μmol of the racemic compound of dimethylsilylene bis{1,1'-(2-ethyl-4-phenyl-4-hydroazulenyl)zirconium dichloride was dissolved in toluene, and the solution was charged into the autoclave together with a high pressure argon gas breaking through the safety rupture disk. The content of the autoclave was heated to 80° C. and the polymerization of propylene was conducted for one hour. Thereafter, unreacted propylene was purged to terminate the polymerization of propylene, thereby obtaining 180 g of polypropylene. As a result of te measurements, it was confirmed that the catalyst activity was 3600 and the complex activity was $17.6 \times 10^4$, and the obtained polypropylene had a melting point (Tm) of 149.2° C., a melt flow rate (MFR) of 11, a weight-average molecular weight (Mw) of $20 \times 10^5$ and a Q-value (Mw/Mn) of 2.5.

(3) Synthesis of dimethylsilylene bis[1,1'-{2-methyl-4-(4-chlorophenyl)-4-hydroazulenyl}] hafnium dichloride 29 ml of a pentane solution containing 47.0 mmol of t-butyl lithium (1.64 M) was dropped into a solution prepared by dissolving 4.5 g (23.53 mmol) of 1-bromo-4-chlorobenzene in a mixed solution composed of 30 ml of n-hexane and 30 ml of diethyl ether at −78° C. The resultant solution was stirred at −5° C. for 1.5 hours, and then mixed with 3.0 g (21.2 mmmol) of 2-methyl azulene to react these components with each other. The reaction solution was stirred for 1 hour while the temperature thereof was gradually raised to room temperature.

Thereafter, the reaction solution was cooled to −5° C., and then mixed with 40 μl (0.47 mmol) of 1-methhylimidazole and then with 1.28 ml (10.59 mmol) of dichlorodimethyl silane. After the reaction solution was stirred at room temperature for 1.5 hours, dilute hydrochloric acid was added thereto to terminate the reaction. The reaction solution was separated into organic and aqueous phases, and the organic phase was concentrated under a reduced pressure. After the solvent is removed, the obtained product was purified by a silica gel column chromatography (a mixed solvent: dichloromethane and n-hexane), thereby obtaining 2.74 g of an amorphous solid product.

Next, the thus-obtained reaction product was dissolved in 20 ml of dry diethyl ether. 6.3 ml of an n-hexane solution containing 9.72 mmol of n-butyl lithium (1.54 M) was dropped into the diethyl ether solution at −78° C. After completion of the dropping, the reaction solution was stirred for 12 hours while the temperature thereof was gradually raised to room temperature. Thereafter, the reaction solution was stirred under a reduced pressure to remove the solvent, and then mixed with 15 ml of a mixed solvent of dry toluene and dry diethyl ether (40:1). After cooling to −78° C., the reaction solution was mixed with 1.56 g (4.86 mmol) of hafnium tetrachloride and the temperature thereof was immediately raised to room temperature, followed by stirring at room temperature for 4 hours. The obtained reaction solution was filtered through celite to separate a solid component therefrom. The thus-obtained solid component was extracted with 90 ml of dichloromethane. The extract was subjected to distillation to remove the solvent therefrom, thereby obtaining 320 ml of a racemic compound of dimethylsilylene bis[1,1'-{2-methyl-4-(4-chlorophenyl)-4-hydroazuleneyl}]hafnium dichloride (yield: 7%).

The chemical shifts of $^1$H-NMR of the above-obtained racemic compound are as follows.

300 MHz, CDCl$_3$ (ppm) δ0.95 (s, 6H, SiMe$_2$), 2.21 (s, 6H, 2-Me), 4.92–4.96 (brd, 2H), 5.70–6.15 (m, 8H), 6.78 (d, 2H), 7.28 (s, 8H, arom).

(4) Polymerization of Propylene

The same procedure as defined in the above item (2) was conducted except that the racemic compound of dimethylsilylene bis[1,1'-{2-methyl-4-(4-chlorophenyl)-4-hydroazulenyl}]hafnium dichloride obtained in the above item (3) was used as the component (A), to obtain 146 g of polypropylene. As a result of the measurements, it was confirmed that the catalytic activity was 2900, the complex activity was $12.0 \times 10^4$, and the obtained polypropylene had a melting point (Tm) of 150.6° C., a melt flow rate (MFR) of 0.4, a weight-average molecular weight (Mw) of $5.6 \times 10^5$ and a Q-value (Mw/Mn) of 3.1.

What is claimed is:

1. A transition metal compound represented by the following general formula (I):

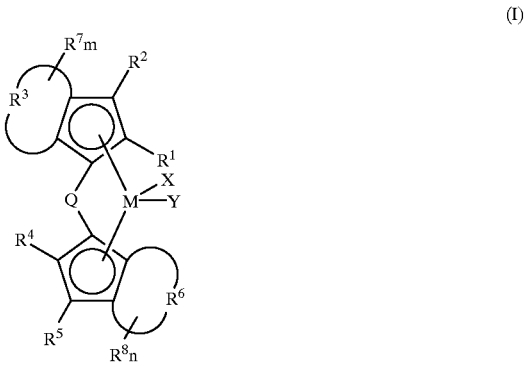

(I)

wherein $R^1$, $R^2$, $R^4$ and $R^5$ each independently represent a hydrogen atom, a $C_{1-10}$ hydrocarbon group, a $C_{1-18}$ silicon-containing hydrocarbon group or a $C_{1-18}$ halogenated hydrocarbon group; $R^3$ and $R^6$ each independently represent a $C_{3-10}$ saturated or unsaturated divalent hydrocarbon group, with the proviso that at least one of $R^3$ and $R^6$ has from 5 to 8 carbon atoms; $R^7$ and $R^8$ each independently represent a $C_{1-20}$ hydrocarbon group, a $C_{7-30}$ oxygen-containing aryl group, a $C_{7-30}$ nitrogen-containing aryl group or a $C_{7-30}$ sulfur-containing aryl group, with the proviso that at least one of $R^7$ and $R^8$ is a $C_{7-30}$ oxygen-containing aryl group, a $C_{7-30}$ nitrogen-containing aryl group or a $C_{7-30}$ sulfur-containing aryl group; m and n each independently represent an integer of from 0 to 20, with the proviso that m and n are not 0 at the same time and if m or n is an integer of not less than 2, R⁷'s or R⁸'s may be connected to each other in arbitrary positions to form a new cyclic structure; Q represents a divalent $C_{1-20}$ hydrocarbon group, a divalent $C_{1-20}$ halogenated hydrocarbon group or a silylene, oligosilylene or germylene group which may have a $C_{1-20}$ hydrocarbon or halogenated hydrocarbon group; X and Y each independently represent a hydrogen atom, a halogen atom, a $C_{1-20}$ hydrocarbon group, a $C_{1-20}$ silicon-containing hydrocarbon group, a $C_{1-20}$ halogenated hydrocarbon group, a $C_{1-20}$ oxygen-containing hydrocarbon group, an amino group or a $C_{1-20}$ nitrogen-containing hydrocarbon group; and M represents a transition metal element belonging to the groups 4 to 6 in the periodic table.

2. The transition metal compound according to claim 1, wherein $R^3$ and $R^6$ each have 5 carbon atoms.

3. The transition metal compound according to claim 1, which is represented by the following general formula (II):

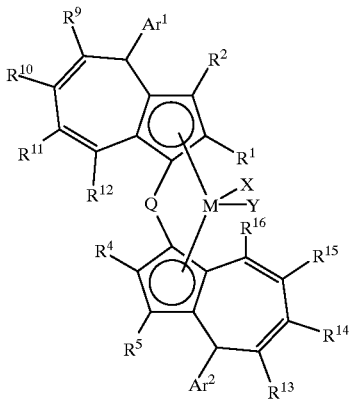

(II)

wherein $R^1$ and $R^4$ each independently represent a $C_{1-6}$ hydrocarbon group, a $C_{1-6}$ silicon-containing hydrocarbon group or a $C_{1-6}$ halogenated hydrocarbon group; $R^2$ and $R^5$ each independently represent a hydrogen atom or a $C_{1-6}$ hydrocarbon group; $R^9, R^{10}, R^{11}, R^{12}, R^{13}, R^{14}, R^{15}$ and $R^{16}$ each independently represent a hydrogen atom or a $C_{1-20}$ hydrocarbon group; $Ar^1$ and $Ar^2$ each independently represent a $C_{7-30}$ oxygen-containing aryl group, a $C_{7-30}$ nitrogen-containing aryl group or a $C_{7-30}$ sulfur-containing aryl group; and Q, M, X and Y are as defined in the general formula (I).

4. The transition metal compound according to claim 3, wherein $Ar^1$ and $Ar^2$ each are a $C_{7-30}$ oxygen-containing aryl group.

5. The transition metal compound according to claim 1, wherein said oxygen-containing aryl group is represented by the following general formula (III) or (IV):

—Ar³—OR¹⁷ (III)

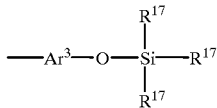

(IV)

wherein $Ar^3$ represents a $C_{6-18}$ aryl group; and $R^{17}$'s may be the same or different and each represent a hydrogen atom, a $C_{1-6}$ alkyl group, a $C_{3-6}$ cycloalkyl group, a $C_{6-10}$ aryl group, a $C_{6-10}$ halogen-containing aryl group; a $C_{6-10}$ nitro group-containing aryl group or a $C_{7-14}$ alkoxyl group-containing aryl group.

6. The transition metal compound according to claim 1, wherein M is a transition metal element belonging to the group 4 in the periodic table.

* * * * *